United States Patent
Li et al.

(10) Patent No.: US 10,019,833 B2
(45) Date of Patent: Jul. 10, 2018

(54) LUGGAGE VISUALIZATION AND VIRTUAL UNPACKING

(71) Applicant: Siemens Corporation, Iselin, NJ (US)

(72) Inventors: Wei Li, Princeton, NJ (US); Gianluca Paladini, Skillman, NJ (US)

(73) Assignee: SIEMENS CORPORATION, Iselin, NJ (US)

( * ) Notice: Subject to any disclaimer, the term of this patent is extended or adjusted under 35 U.S.C. 154(b) by 182 days.

(21) Appl. No.: 14/383,210

(22) PCT Filed: Mar. 7, 2013

(86) PCT No.: PCT/US2013/029494
§ 371 (c)(1),
(2) Date: Sep. 5, 2014

(87) PCT Pub. No.: WO2013/142072
PCT Pub. Date: Sep. 26, 2013

(65) Prior Publication Data
US 2015/0022522 A1    Jan. 22, 2015

Related U.S. Application Data

(60) Provisional application No. 61/613,037, filed on Mar. 20, 2012.

(51) Int. Cl.
*G06T 17/00* (2006.01)
*G06T 15/08* (2011.01)
(Continued)

(52) U.S. Cl.
CPC ........... *G06T 15/08* (2013.01); *G01N 23/046* (2013.01); *G06T 19/00* (2013.01);
(Continued)

(58) Field of Classification Search
CPC ..... A45C 9/00; A45C 2003/008; A45C 15/00; A45C 7/0086; A45C 5/14; A45C 5/03;
(Continued)

(56) References Cited

U.S. PATENT DOCUMENTS

| | | | |
|---|---|---|---|
| 2008/0253653 A1* | 10/2008 | Gable | G01V 5/0008 382/173 |
| 2009/0034790 A1* | 2/2009 | Song | G06T 7/0002 382/103 |

(Continued)

FOREIGN PATENT DOCUMENTS

| | | |
|---|---|---|
| CN | 1272625 A | 11/2000 |
| CN | 1708686 A | 12/2005 |
| CN | 102099708 A | 6/2011 |

OTHER PUBLICATIONS

International Search Report; Application No. PCT/US2013029494, Filing Date: Mar. 7, 2013; 6-pages.
(Continued)

*Primary Examiner* — Xilin Guo

(57) ABSTRACT

Methods and systems for luggage visualization perform virtual unpacking by visually moving an object image away from its original pose. A scanned 3D volume is segmented guided by a confidence measure to create a label volume whose voxels specify the detected object IDs. The luggage dataset and the label volume are visualized by volume rendering. Using an automatic coloring algorithm, any pair of objects whose projections are adjacent in an image are assigned distinct hues. A layered framework efficiently renders a scene mixed with packed luggage, animated unpacking objects, and already unpacked objects put aside for further inspection. A GPU is used to automatically select objects that are not blocked by others and can be unpacked.

18 Claims, 33 Drawing Sheets

(51) Int. Cl.
    *G06T 19/00*     (2011.01)
    *G01N 23/046*     (2018.01)

(52) U.S. Cl.
    CPC ... *G01N 2223/419* (2013.01); *G01N 2223/42* (2013.01); *G01N 2223/639* (2013.01); *G01N 2223/643* (2013.01); *G06T 2207/10072* (2013.01); *G06T 2207/30112* (2013.01)

(58) Field of Classification Search
    CPC ....... A45C 13/03; A45C 13/02; A45C 7/0031; A45C 2013/026; A45C 13/10; G01N 23/04; G01N 23/043; G01N 2001/022; G01N 27/622; G01V 5/0008; G01V 8/10; A61B 6/5205; A61B 6/4028; G06K 2209/09; G06K 9/00201; G06K 9/00228; G06K 9/002; G06T 15/08; G06T 2207/30112; G06T 2207/10081; G06T 2200/04; G06T 7/0002; G06T 7/10; B64F 1/366

See application file for complete search history.

(56) References Cited

U.S. PATENT DOCUMENTS

| | | | |
|---|---|---|---|
| 2010/0046704 A1 | 2/2010 | Song et al. | |
| 2010/0316268 A1* | 12/2010 | Liang | G06T 19/00 382/128 |
| 2011/0054295 A1* | 3/2011 | Masumoto | A61B 5/055 600/407 |
| 2011/0069066 A1* | 3/2011 | Engel | G06T 15/08 345/424 |
| 2011/0188751 A1* | 8/2011 | Litvin | G06T 7/155 382/173 |
| 2011/0235883 A1* | 9/2011 | Nakagawa | G06T 7/12 382/131 |
| 2012/0099777 A1* | 4/2012 | Ying | G06T 7/0081 382/131 |
| 2012/0182392 A1* | 7/2012 | Kearns | B25J 11/009 348/46 |
| 2013/0238288 A1* | 9/2013 | Rolleston | G06Q 30/06 703/1 |

OTHER PUBLICATIONS

Wilmot Li et al: "Automated Generation of Interactive 3D Exploded View Diagrams" Youtube Video; www.youtube.com/match?v=nHTUbjjREte, Sep. 21, 2009; retrieved from Internet by Applicant on May 3, 2016; Note entire video, more specifically 2:43-3:15.

PCT Search Report dated Sep. 26, 2014 corresponding to PCT International Application No. PCT/US2013/029494 filed Mar. 7, 2013 (6 pages).

Report of Examination dated Aug. 5, 2016; Chinese Patent Application No. 201380026101.X; Filing Date: Mar. 7, 2013; 19 pages.

\* cited by examiner

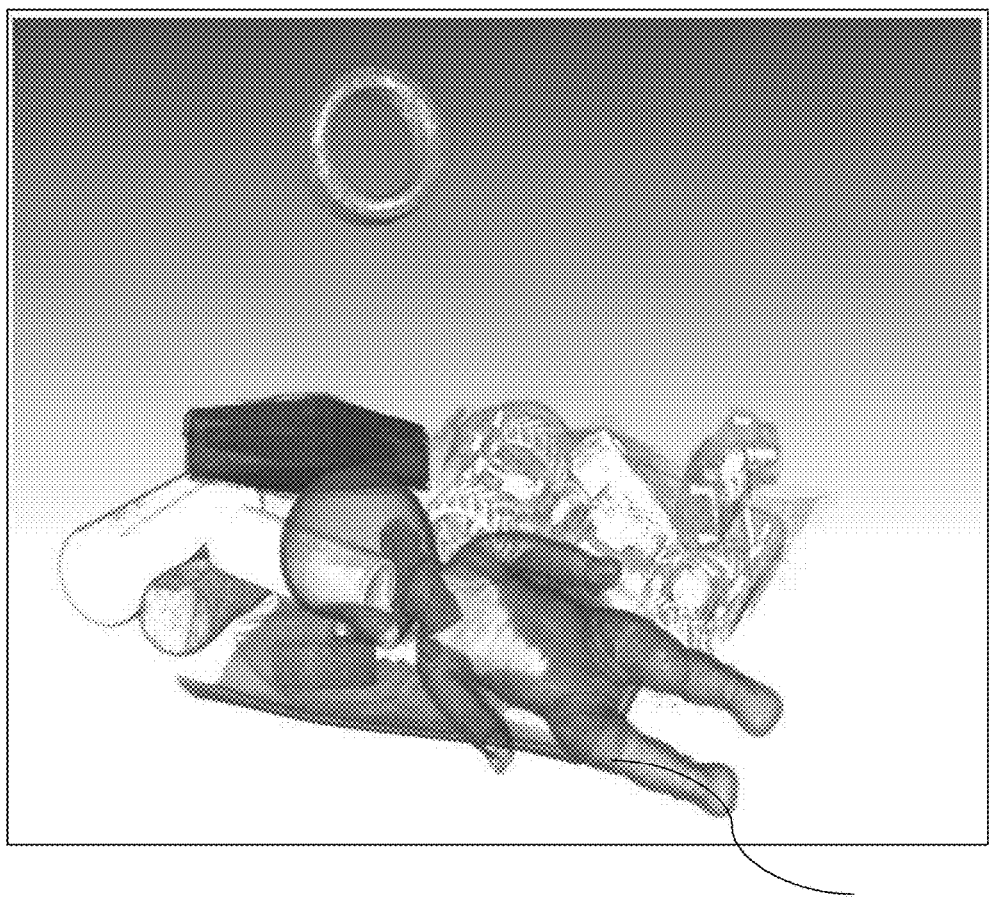
FIG. 1B     101

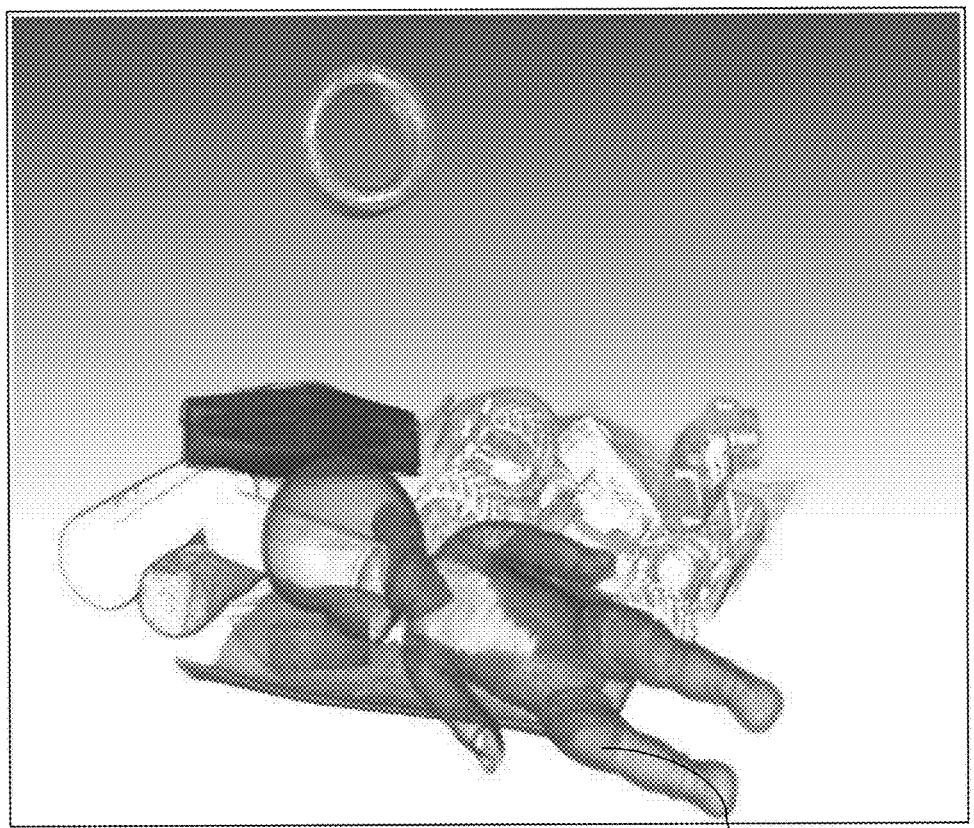
FIG. 1C     101

101

401

402

403

404

1203

1201

LUGGAGE VISUALIZATION AND VIRTUAL UNPACKING

STATEMENT OF RELATED CASES

The present application claims priority to and the benefit of U.S. Provisional Patent Application Ser. No. 61/613,037 filed on Mar. 20, 2012, which is incorporated herein by reference in its entirety.

TECHNICAL FIELD

The present invention relates to methods and systems to inspect luggage by using imaging techniques. More in particular it relates to methods and systems to visualize contents of a piece of luggage by virtually and graphically unpacking closely packed objects in the piece of luggage by a computer.

BACKGROUND

Luggage screening is unavoidable for either checked-in luggage or carried-on baggages in order to detect threaten and forbidden items, which is especially true for aviation security. The most trustable way is still physically opening the luggage and unpacking its contents. This unfortunately is very inefficient and intrusive.

With modern scanning technology, such as computed tomography (CT), it is possible to reconstruct accurate three-dimensional geometric properties of scanned luggage and its contained objects. Naturally, a luggage is packed, which means that many objects are in close contact with each other and appear connected, overlapping and cluttered when visualized in a scanned image. It usually involves human interaction to unpack and isolate individual objects for better inspection.

Accordingly, improved and novel methods and systems that virtually unpack objects that are closely packed in luggage and display the unpacking and the unpacked objects on a computer screen are required.

SUMMARY

In accordance with an aspect of the present invention systems and methods are provided for viewing on a display a virtual unpacking of luggage containing objects in a packed state into objects in an unpacked state, wherein images are created from volumetric data of physical luggage obtained with a scanner and images of the objects in unpacked state are displayed simultaneously on the display.

In accordance with an aspect of the present invention a method is provided to virtually unpack luggage, comprising a scanner obtaining three-dimensional (3D) volumetric data of a plurality of objects in a packed state inside the luggage, a processor processing the 3D volumetric data to segment the plurality of objects in the packed state into a plurality of 3D volume objects corresponding to the plurality of packed objects and the processor rendering each of the plurality of 3D volume objects in an unpacked state to be simultaneously displayed on a display.

In accordance with a further aspect of the present invention a method is provided, wherein the objects in the packed state are unpacked in an order based on a state of occlusion of the packed objects relative to a view direction used to visualize the packed objects.

In accordance with yet a further aspect of the present invention a method is provided, wherein a rendered image of each of the plurality of unpacked 3D volume objects is stored in a memory as an individually retrievable sprite.

In accordance with yet a further aspect of the present invention a method is provided further comprising: the processor segmenting the plurality of packed objects from the 3D volumetric image to create a plurality of binary label volumes corresponding to the packed objects and the processor combining the binary volumes to form a label volume with a voxel storing an identification (ID) value of a corresponding binary label volume.

In accordance with yet a further aspect of the present invention a method is provided, further comprising: the processor generating an assignment of colors to each segmented object by computing an interference map from object identification (ID) images.

In accordance with yet a further aspect of the present invention a method is provided, wherein the interference map is calculated by the processor through a 2D filtering by evaluating an expression:

$$\min_{layer(pA) \leq LT \wedge layer(pB) \leq LT} (DIST(Pa, Pb)) \leq DT,$$

with pA and pB representing pixels in an image projected from front faces of objects A and B respectively, dist(pA, pB) represents a distance between the two pixels in image space, DT is a predetermined distance threshold, layer(p) represents a layer index of pixel p, and LT restricts computation to LT layers and utilizing a graph coloring algorithm to assign a different hue to each interfering objects in the interference map.

In accordance with yet a further aspect of the present invention a method is provided, further comprising: the processor applying the object ID images of a plurality of segmented objects to determine an unpacking order based on an occlusion ratio of each object from a given viewing direction.

In accordance with yet a further aspect of the present invention a method is provided, wherein an unpacking scene is rendered by accessing at least three rendering layers, wherein a first layer containing a rendered image of all objects that are in a packed state, a second layer containing a rendered image of an object being unpacked and a third layer containing rendered images of sprites of unpacked objects.

In accordance with another aspect of the present invention a system is provided to display virtually unpacking of luggage containing a plurality of objects in a packed state, comprising a luggage scanner to obtain three-dimensional (3D) volumetric data of the plurality of objects in the packed state inside the luggage, a memory enabled to store data and instructions, a processor enabled to access the memory to obtain data and instructions, the processor enabled to execute instructions to perform the steps: accessing the 3D volumetric data generated by the luggage scanner, processing the 3D volumetric data to segment the plurality of objects in the packed state into a plurality of 3D volume objects corresponding to the plurality of packed objects and rendering each of the plurality of 3D volume objects in an unpacked state to be simultaneously displayed on a display.

In accordance with yet another aspect of the present invention a system is provided, wherein the plurality of objects in the packed state are unpacked by the processor in an order based on a state of occlusion of the plurality of objects in the packed state relative to a view direction used to visualize the objects.

In accordance with yet another aspect of the present invention a system is provided, wherein the processor is further enabled to perform the step: segmenting the plurality of objects in the packed state from the 3D volumetric data to create a binary label volume for each of the plurality of objects in the packed state.

In accordance with yet another aspect of the present invention a system is provided, further comprising: the processor enabled to generate a 3D label volume containing object ID labels for a plurality of segmented objects, wherein each volume sample corresponds to an object ID of a related segmented binary label volume.

In accordance with yet another aspect of the present invention a system is provided, further comprising: the processor enabled to generate an assignment of colors to each segmented object, by rendering object ID images for each object where each pixel in the ID image corresponds to one segmented object index, and by computing an interference map from object ID images through a 2D filtering by evaluating an expression $$\min_{layer(pA) \le LT \wedge layer(pB) \le LT} (DIST(Pa, Pb)) \le DT,$$

with pA and pB representing pixels in an image projected from front faces of objects A and B respectively, dist(pA, pB) represents a distance between the two pixels in image space, DT is a predetermined distance threshold layer(p) represents a layer index of pixel p, and LT restricts computation to LT layers and utilizing a graph coloring algorithm to assign a different hue to each interfering objects in the interference map.

In accordance with yet another aspect of the present invention a system is provided, further comprising: the processor enabled to apply the object ID images of the plurality of segmented objects to determine an unpacking order based on an occlusion ratio of each object relative to a viewing direction.

In accordance with yet another aspect of the present invention a system is provided, further comprising a display to render the unpacking as an animated series of images.

In accordance with yet another aspect of the present invention a system is provided, further comprising: the processor enabled to render an unpacking scene by accessing at least three rendering layers, wherein a first layer containing a rendered image of all objects that are in a packed state, a second layer containing a rendered image of an object being unpacked and a third layer containing rendered images of sprites of unpacked objects.

In accordance with yet another aspect of the present invention a system is provided, wherein images of unpacked objects are animated in an order that displays a repacking of the objects in the unpacked state to the plurality of objects in the packed state.

In accordance with a further aspect of the present invention a method is provided for visual unpacking on a display three-dimensional (3D) volumetric data of a plurality of objects in a packed state into a plurality of unpacked objects, comprising: a processor processing the 3D volumetric data to segment the plurality of objects in the packed state into a plurality of 3D volume objects corresponding to the plurality of packed objects and the processor rendering each of the plurality of 3D volume objects in an unpacked state to be simultaneously displayed on the display, wherein the objects in the packed state are unpacked in an order based on a state of occlusion of the packed objects in an unpacking direction.

In accordance with yet a further aspect of the present invention a method is provided, wherein objects are unpacked in a direction opposite a viewing direction.

In accordance with yet a further aspect of the present invention a method is provided, wherein the method is applied in a luggage inspection system.

DRAWINGS

FIGS. 1A-1H illustrate virtual unpacking of objects in according with various aspects of the present invention;

DESCRIPTION

Methods and systems are provided herein in accordance with various aspects of the present invention to implement a visualization work flow to assist with luggage screening. A volumetric representation of a luggage piece is segmented into meaningful real-world objects. The segmented objects are automatically assigned distinguishable colors based on their overlapped proximity, as well as opacities depending on the viewing parameters.

The original luggage volume, the segmentation results, and the automatically assigned colors are fed into a volume rendering system. For any user defined viewing direction, objects that can be unpacked are determined and unpacking is visualized, for instance on a computer screen, by showing an animated transition of the objects flying from its original position to a unpacking destination. Unpacked objects can be manipulated individually, such as rotating, changing transfer function, etc, for inspection.

The system keeps packed luggage, already unpacked objects, and the objects in transition in the same scene and allows repacking (packing the unpacked objects back into their original position within the luggage).

The term object is used herein. Real luggage contains real physical objects. In accordance with an aspect of the present invention a three dimensional (3D) volumetric representation of the piece of luggage that contains the physical object is created by applying 3D volume segmentation. Accordingly a segmented 3D object (for instance a 3D volumetric representation or 3D rendered image) is created from the actual physical object. Aspects of the present invention are focused on virtual or graphical unpacking of an image rendering of the luggage and not on the physical unpacking of the luggage. Accordingly, the terms object and luggage herein relate to image renderings of an object and the luggage, unless it is clear from the context that physical objects and luggage are intended.

The term "unpackable object" is also used herein. We define an unpackable object as an object which can be unpacked, where being unpacked means being moved from a cluttered location packed within the luggage to an uncluttered location outside of the luggage.

Figure 1A:
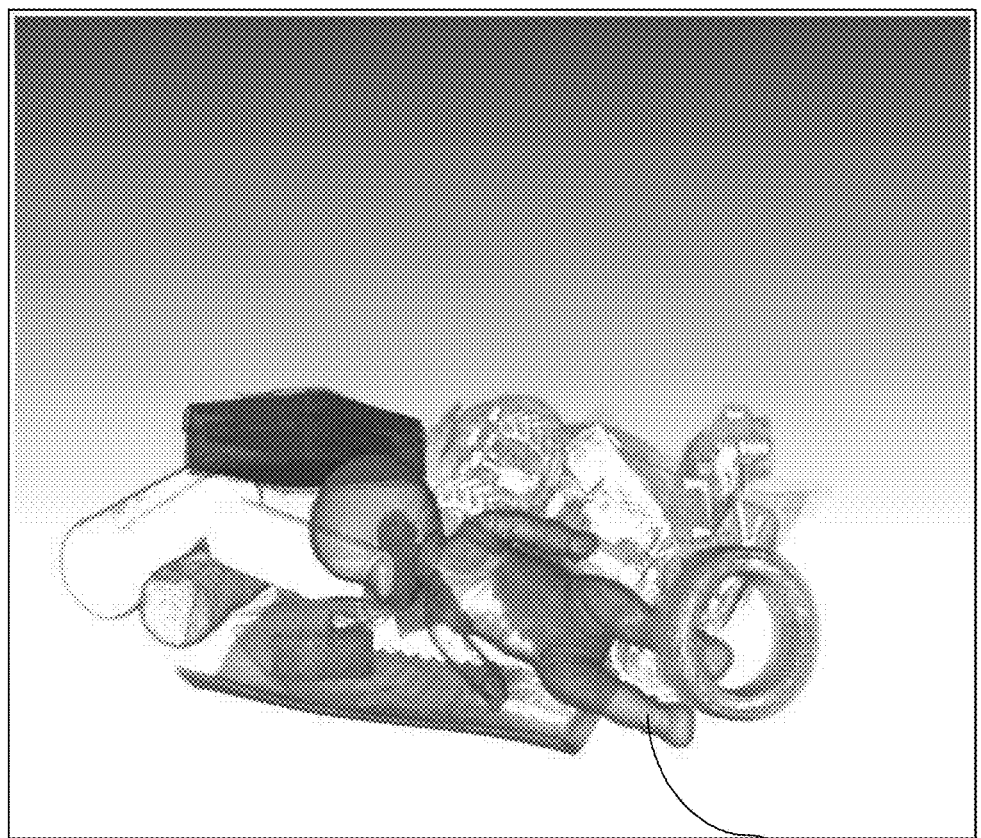
Figure 1D:
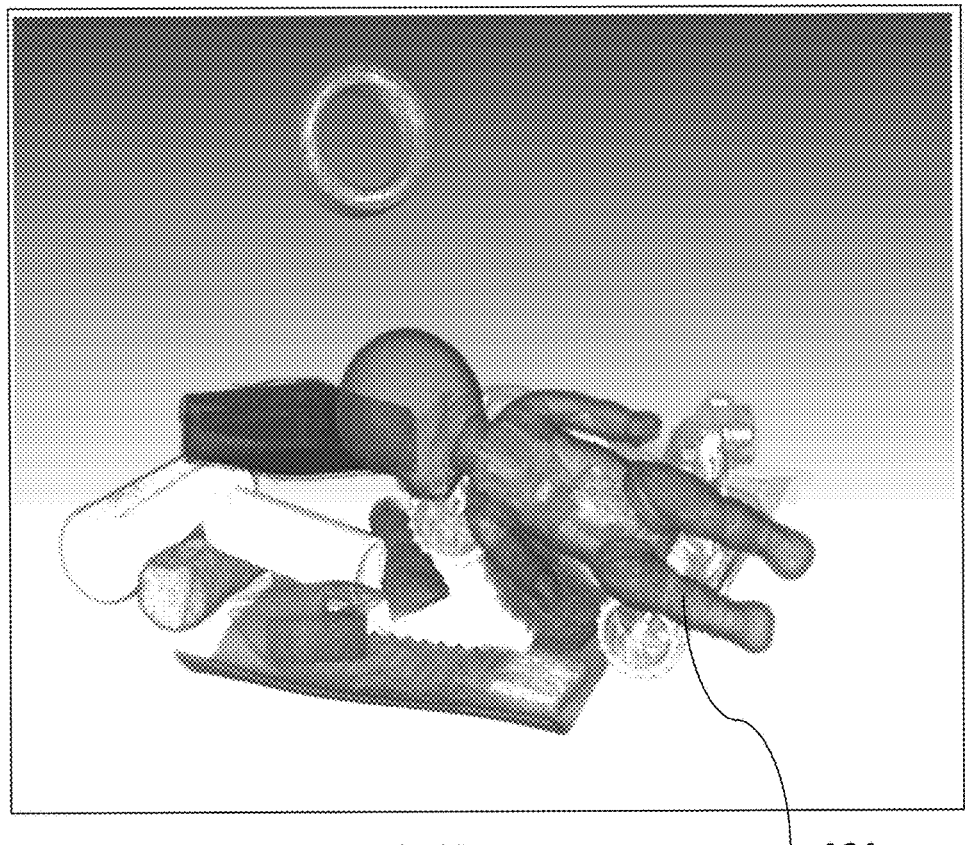
Figure 1E:
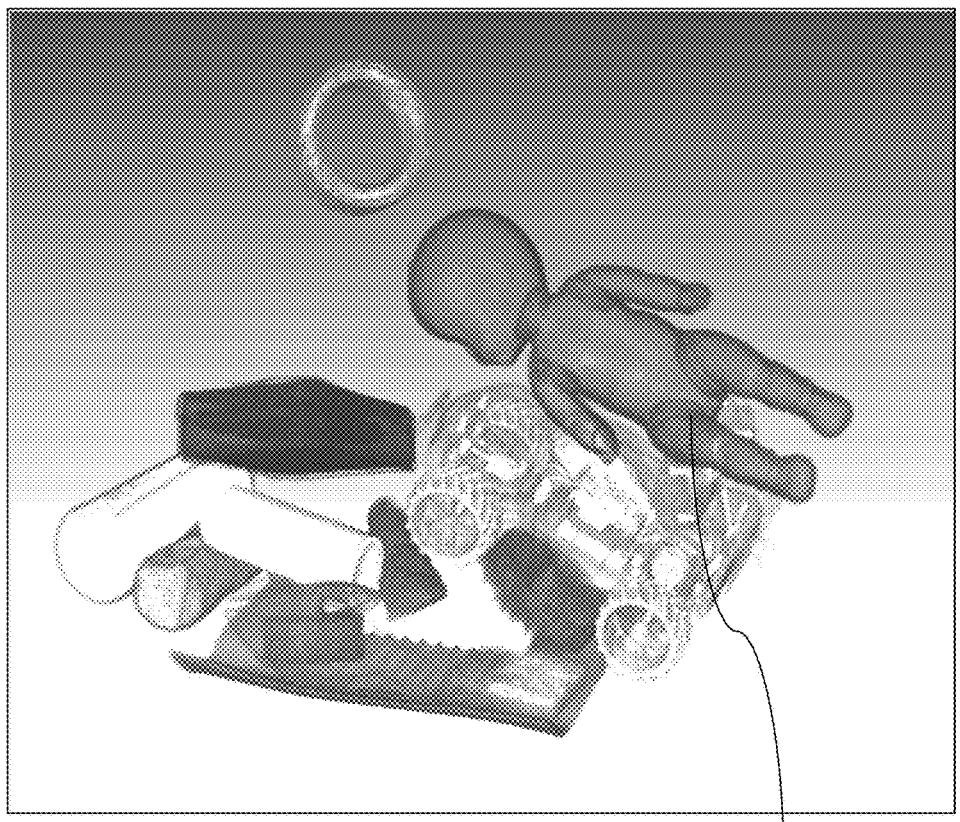
Figure 1F:
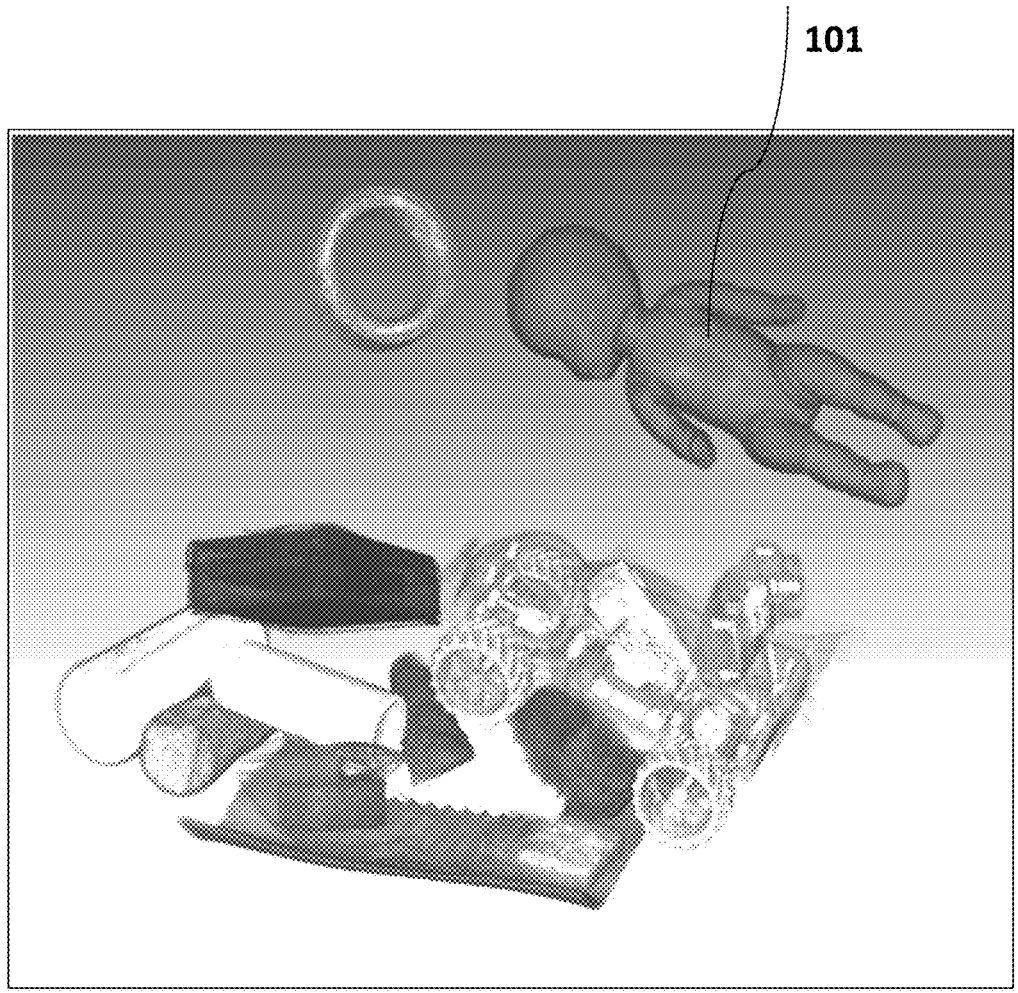
Figure 1G:
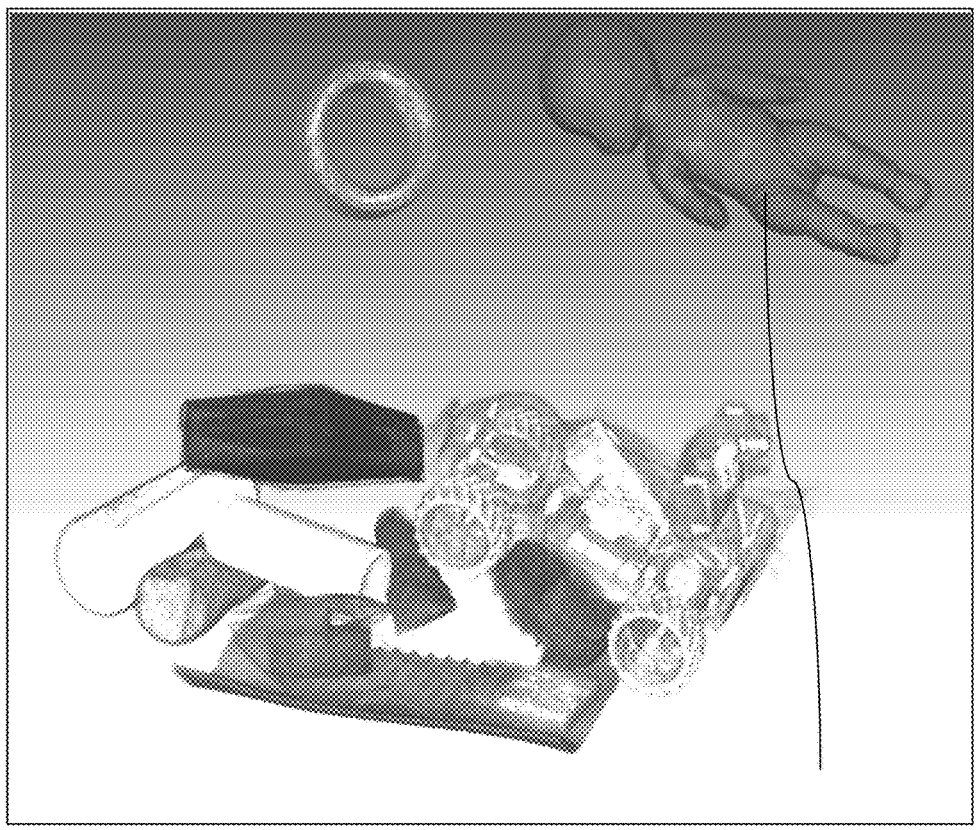
Figure 1H:
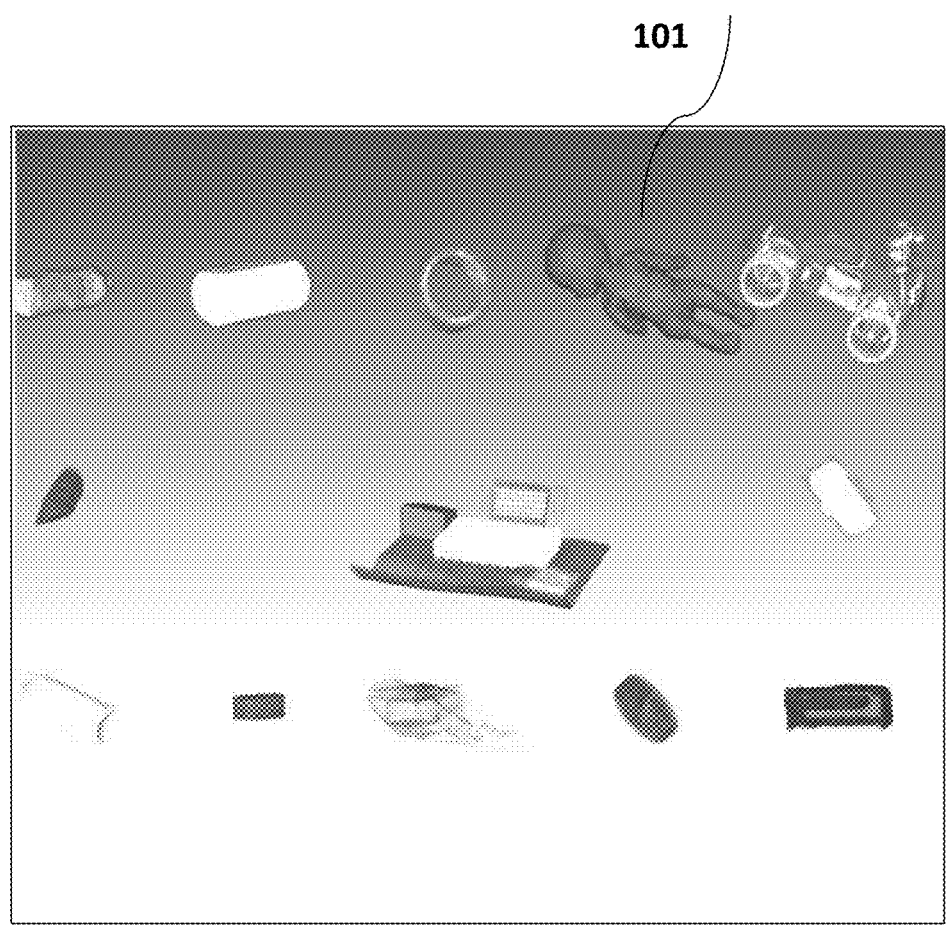

FIG. 1 illustrates capabilities of the systems and methods of the present invention, where FIG. 1A is a volume rendition of a segmented CT scan of luggage. By comparing FIGS. 1A-1H, one can observe how the doll 101 automatically moves first towards the eye, then flies to the top right corner of the image. FIG. 1H presents a scene where many objects have moved to their unpacked positions.

In accordance with an aspect of the present invention, systems and methods are provided to segment luggage into luggage objects utilizing a state-of-the-art graph partitioning approach, as for instance, described in "GRADY, L., AND SCHWARTZ, E. L. 2006. Isoperimetric graph partitioning for image segmentation. IEEE Transactions on Pattern Analysis and Machine Intelligence 28, 3 (March), 469-475" enhanced by a confidence measure of the quality of a segmentation. The confidence measure gives high scores to semantic meaningful real-world objects that are homogeneous and have well-defined boundaries against the surrounding segments, and it guides the segmentation algorithm to recursively split connected objects in an input volume until the segmentation quality can't be improved any more.

In order to assign distinct colors to objects appearing adjacent in an image, the system first generates an image of superimposed object IDs, from which whether any pair of objects interfering with each other is determined. A modified graph coloring algorithm is then performed to ensure that any interfering pair are assigned distinguishable hues while the hue space is fully exploited. In order to enhance the perceived visibility of individual objects, a tinting approach is adopted, in which the hues automatically assigned to an object can be modulated individually for each object based on an opacity transfer function, but can also be modulated by a master transfer function that affects the overall opacity of all objects. The ability to vary these combined opacity controls allow the user not only to inspect the object's shape and color, but also to evaluate an object's composition, for example an object's density based on a Hounsfield scale in CT scanned data.

To virtually unpack a luggage, instead of physically partitioning the original volume into separate volumes for each segmented object, which would increase computer memory storage requirements considerably, volume rendering is performed in multiple passes by using the original volume and varying the transfer function and geometric transformation in each pass, in order to render only the desired visible objects at the desired location. The result of multiple rendering passes is composited together into a final image.

A brute-force design for volume rendering in multiple passes requires the number of rendering passes equals to that of the objects in the worst case. This obviously is too computationally expensive considering a typical luggage contains several dozens of objects. To efficiently visualize unpacking, the whole scene in accordance with an aspect of the present invention is divided into three layers: packed objects, unpacked objects, and the animation of objects being unpacked or restored. Each layer represents objects being rendered in a particular state as well as caches and displays the previous rendered images to avoid unnecessary repeated rendering. The third layer representing the animation of objects being unpacked is further decomposed into a set of 3D sprites to minimize memory usage and improve rendering performance. A 3D sprite is defined as a 2D rendering of a 3D object, which is cached and visualized always oriented perpendicular to the viewing direction. The animation of such sprites along a path that only involves translation and scaling can create the illusion of a moving 3D object being visualized, while greatly reducing rendering computations.

Next is a listing of various aspects of the present invention:

a. Virtual unpacking or graphical unpacking is provided, which is believed not to have been presented in the literatures. The unpacking herein is the animated visual separation of image objects, very much like one would perform in the physical unpacking of objects in a physical piece of luggage. This is different from the "peeling" of objects in an image, such as a 3D image created by for instance a CT scan. This "peeling" is known from medical imaging, wherein for instance images of organs or bones inside the skin of a patient are revealed to the observer by making other occluding volume data invisible. The virtual unpacking (and if desired, repacking) animated motion provides useful spatial cues about how each object was packed in relation to other objects in its proximity, thereby improving the observer's ability to identify possible mistakes that may have occurred during the segmentation step.

b. An automatic tinting approach is provided which provides an optimal choice of colors, as well as avoiding unsmoothness across object boundaries.

c. The graph coloring algorithm has been customized to automatically assign colors to conflicting objects while fully utilizing the color space.

d. Two GPU accelerated methods are provided for determining unpackable objects that are not blocked by others.

e. A layered framework efficiently renders a scene mixed with packed luggage, animated unpacking objects, and already unpacked objects put aside for further inspection.

Related work is reviewed and luggage segmentation is described, followed by a description of luggage visualization and virtual unpacking which is followed by a description of implementation details and results.

Related Work

Transfer Function Design

One aspect of a system provided herein is that it automatically assigns colors to different objects, which can be considered as a simplified version of automatic transfer function generation, which has been a popular topic and has attracted numerous publications, for instance "[18] ZHOU, J., AND TAKATSUKA, M. 2009. Automatic transfer function generation using contour tree controlled residue flow model and color harmonics. IEEE Transactions on Visualization and Computer Graphics 15, 6 (November), 1481-1488" and "[5] CHAN, M.-Y., WU, Y., MAK, W.-H., CHEN, W., AND QU, H. 2009. Perception-based transparency optimization for direct volume rendering. IEEE Transactions on Visualization and Computer Graphics 15, 6 (November), 1283-1290." Most of these works focus on adjusting the color and opacity of the transfer function so that different structures in a volume can be visualized. Adjusting color and opacity is a common way of highlighting different properties of the material composition of structures within scanned volumetric data, for example soft tissue vs. bone in medical datasets.

Luggage visualization herein relies on unpacking to reveal occluded parts of an object and it is desirable for each object to have a consistent appearance. Besides, without additional information, each object is considered equally important.

Some previous work of transfer function design also have an emphasis on aesthetics, such as assigning realistic colors. In contrast, the focus herein is on the distinguishability of the shape of an object from its background and other objects in its proximity, and so it is preferred to assign distinct hues to neighboring objects.

Exploded Views

When an object is virtually unpacked from the luggage, it is visualized as moving away from the luggage and being placed in a location where the object can be inspected free of any clutter near it. In a preferred embodiment of the present invention, the automatic determination of such uncluttered location is based on "exploded views", a technique commonly used by illustrators in order to visualize complex mechanical assemblies. The generation of exploded views in Virtual Unpacking can be considered related to but different from the generation of exploded views of volumetric datasets (as described in "BRUCKNER, S., AND GRÖLLER, M. E. 2006. Exploded views for volume data. IEEE Transactions on Visualization and Computer Graphics 12, 5 (9), 1077-1084"), in which a volumetric dataset is cut into partitions and displaced to reveal hidden details, or the generation of exploded views of geometric datasets (as described in "[15] LI, W., AGRAWALA, M., CURLESS, B., AND SALESIN, D. 2008. Automated generation of interactive 3d exploded view diagrams. In ACM SIGGRAPH, 101:1-101:7"), in which a mechanical assembly is split based either on a known assembly sequence order or computed based on contact, blocking and containment relationships among parts.

Each exploded part is either a portion of an organic object or designed to be assembled into a model of multiple parts. In exploded views, the context of each partition is extremely important and should be carefully preserved, and its explosion path is highly restricted. In contrast, for a packed luggage, there is usually no meaningful correlation between objects, and there is much more freedom in relocating them. Therefore a system as provided herein in accordance with at least one aspect of the present invention prioritizes removing occlusion over keeping context, although it reserves the capability of restoring any unpacked object to its original position to deal with possible inaccuracy in a segmentation.

Visibility Sorting and Collision Detection

The unpackable object determination has a very limited similarity to GPU accelerated visibility sorting as described in "[8] GOVINDARAJU, N. K., HENSON, M., LIN, M. C., AND MANOCHA, D. 2005. Interactive visibility ordering and transparency computations among geometric primitives in complex environments. In Interactive 3D Graphics and Games, 49-56", "[4] CALLAHAN, S., COMBA, J., SHIRLEY, P., AND SILVA, C. 2005. Interactive rendering of large unstructured grids using dynamic level-of-detail. In IEEE Visualization, 199-206" and collision detection "[7] GOVINDARAJU, N. K., REDON, S., LIN, M. C., AND MANOCHA, D. 2003. Cullide: interactive collision detection between complex models in large environments using graphics hardware. In Graphics hardware, 25-32" in that all utilize a GPU to resolve the spatial relationship among primitives.

In principle, an object is unpackable if it is fully visible in an orthogonal projection and can be unpacked by moving the object towards the observer, opposite to the viewing direction. Naively, such a visibility order can be used as the unpacking order for any desired viewing direction. In the present case, the unpacking direction can be frequently changed according to an inspector's interest. Therefore the unpacking method is customized to only search for the objects taking the first place in the visibility order. Also an occlusion ratio is used to deal with the situation that no object is fully unblocked. Similar to the mentioned references, the multi-pass method as provided herein uses occlusion queries to retrieve the results of depth comparison of the rasterized primitives. Also a single pass algorithm is provided that does not require an occlusion query.

Luggage Segmentation

The foundation of the approach herein for partitioning a luggage volume into meaningful real-world objects is image segmentation as is known in many forms to one of ordinary skill. In one embodiment of the present invention the isoperimetric graph partitioning as described in "[10] GRADY, L., AND SCHWARTZ, E. L. 2006. Isoperimetric graph partitioning for image segmentation. IEEE Transactions on Pattern Analysis and Machine Intelligence 28, 3 (March), 469-475" is applied. However, any of the known image segmentation methods that work on volumetric image data can be applied herein. On top of that, an extension is utilized that is described in "[11] GRADY, L., SINGH, V., KOHLBERGER, T., ALVINO, C., AND BAHLMANN, C. 2012. Automatic segmentation of unknown objects, with application to baggage security. In European Conference on Computer Vision (ECCV)" and that computes the confidence of the quality of a volume segmentation that can be applied as an additional feature in an embodiment of the present invention.

The focus herein is luggage visualization. Therefore, only the major steps of the luggage segmentation approach are outlined. Please see "[11] GRADY, L., SINGH, V., KOHLBERGER, T., ALVINO, C., AND BAHLMANN, C. 2012. Automatic segmentation of unknown objects, with application to baggage security. In European Conference on Computer Vision (ECCV)" as one example of image segmentation.

To obtain a confidence measure, the algorithm annotates a large number of good segments that are homogeneous and have well defined boundaries with the surrounding segments. The annotated segments are then fed into a model learning pipeline to train a confidence measure. After annotation, various features are computed, that include geometric properties (such as surface smoothness, curvature volume) and appearance properties based on density distribution (such as average L1 gradient, average L2 gradient, median and mean intensities). The approach also uses boundary based features such as the total cost of the cuts for isolating this segment from neighboring segments. All the features are invariant to rotation and translation.

Each feature is further normalized to make it invariant to scale and object types. A statistical normalization is also performed by first computing the mean and the standard deviation for all the features over all segments followed by normalizing the feature scores by subtracting the mean and dividing by the standard deviation. Next, the method uses Principal Component Analysis (PCA) to reduce the dimensionality of the data. In a final stage, a Mixture of Gaussian model is fit over the PCA coefficients of all the segments in the training set to approximate the distribution of the good segments in the feature space. Once having a confidence measure, for any given luggage segmentation, the approach computes the PCA coefficients vector from the segmentation's normalized feature vector. Then a confidence score is obtained by calculating the likelihood of the coefficient vector using the Mixture of Gaussian stored in the segment oracle.

To perform luggage segmentation, first, a generic segmentation algorithm such as for instance described in "[9] GRADY, L., AND ALVINO, C. The piecewise smooth mumfordshah function on an arbitrary graph. IEEE Transactions on Image Processing 18, 11, 2547-2561" provides an initial segmentation that roughly separates all the target objects inside the luggage from the background voxels. A subsequent connected component analysis then assigns not-connected foreground segments different labels. Since most of them are still strong under-segmented, i.e. cover groups of target objects, a recursive splitting algorithm is run for each of those individual foreground segments.

For every undersegmented region, the isoperimetric algorithm generates several different plausible binary separations. The confidence measure then is used in conjunction with the isoperimetric ratio to decide if any of the proposed splits generates sub-groups of objects that are sufficiently close to individual objects.

Luggage Visualization

Volume Rendering with Tinted VOIs

Volume rendering combined with masks specifying volume-of-interests (VOI) have been extensively deployed in volume visualization. These VOIs are assigned optical properties different from the rest of the volume, so that they are clearly distinguishable. Typically, each VOI is associated with a full color lookup table as described in "[13] HADWIGER, M., BERGER, C., AND HAUSER, H. 2003. High quality two-level volume rendering of segmented data sets on consumer graphics hardware. Visualization, 301-308", which provides the most flexibility in adjusting the appearance of the VOI.

It is a challenging task to figure out the true color of each segmented object from a gray volume. Note that an artificial object may be built with arbitrary optical properties, which is different from medical visualization. In this case, a requirement is that the shape of each individual object is clearly recognizable, whereas it is acceptable if the object is rendered with colors and opacities different from its true appearance. Sometimes, it is even undesirable to assign an object its true color. For example, if two objects of similar colors overlap in an image, one would like them to be rendered with contrast colors.

The segmentation masks generated as disclosed earlier are non-overlapping binary volumes. That is, each voxel of the original gray volume can only belong to a single VOI, and all sub-voxel boundaries are rounded to the nearest voxel borders. All the binary volumes are combined to form a label volume with each of its voxel storing the ID value ($\geq 1$) of the corresponding binary volume, or an ID value of zero for background. Obviously, it is meaningless to interpolate between different IDs. Therefore the label volume should be sampled with the nearest neighbor method.

The system relies on interpolated samples from the original density volume and proper opacity assignment in the transfer function to hide the unsmoothness of the boundaries of the binary masks. This requires the opacity of the transfer function to be C0 continuous. Obviously, there is no guarantee of such a property if each VOI is associated with an independent color lookup table as in "[13] HADWIGER, M., BERGER, C., AND HAUSER, H. 2003. High quality two-level volume rendering of segmented data sets on consumer graphics hardware. Visualization, 301-308."

Consequently, the following tinting approach was chosen for the luggage visualization as provided herein in accordance with an aspect of the present invention.

a. A master transfer function with C0 continuous opacities is assigned to the whole volume. The colors of the transfer function are preferably but not necessarily gray.
b. Each visible VOI is assigned a tinting color that is multiplied onto the color obtained from the master transfer function for the samples falling into the VOI.
c. If a VOI is set to be hidden, the corresponding tinting color and opacity are set to (0, 0, 0, 0).

Note that hiding a VOI can introduce opacity discontinuity in the transfer function. Hence the blockiness of the binary masks can be noticeable if two objects have touched a boundary of significant area and one of them is hidden. Fortunately, this situation is rare even in a tightly packed luggage. The opacities and colors of the transfer function can be changed dynamically to highlight objects of interest while keeping the tinting unchanged.

Color Optimization

A typical piece of luggage such as a suitcase contains dozens of objects of various sizes. There are many overlaps of the objects in a projected 2D image. Color assignment to make overlapped objects visually separable should be utilized. A natural choice is to use as many colors as the number of objects, and assign the colors either sequentially or randomly. However, it is difficult to distinguish two different but similar colors. The situation is made worse by rendering effects, such as alpha-blending, shading, and transparency.

If two objects are desired to have distinguishable colors, they are declared as mutually interfering. Graph coloring is adopted in which each object is represented as a vertex, and any two interfering objects are connected by an edge. If the dataset can be viewed from an arbitrary angle, any two objects can potentially interfere. Therefore, it is rational to perform view-dependent color assignment.

Figure 2A:
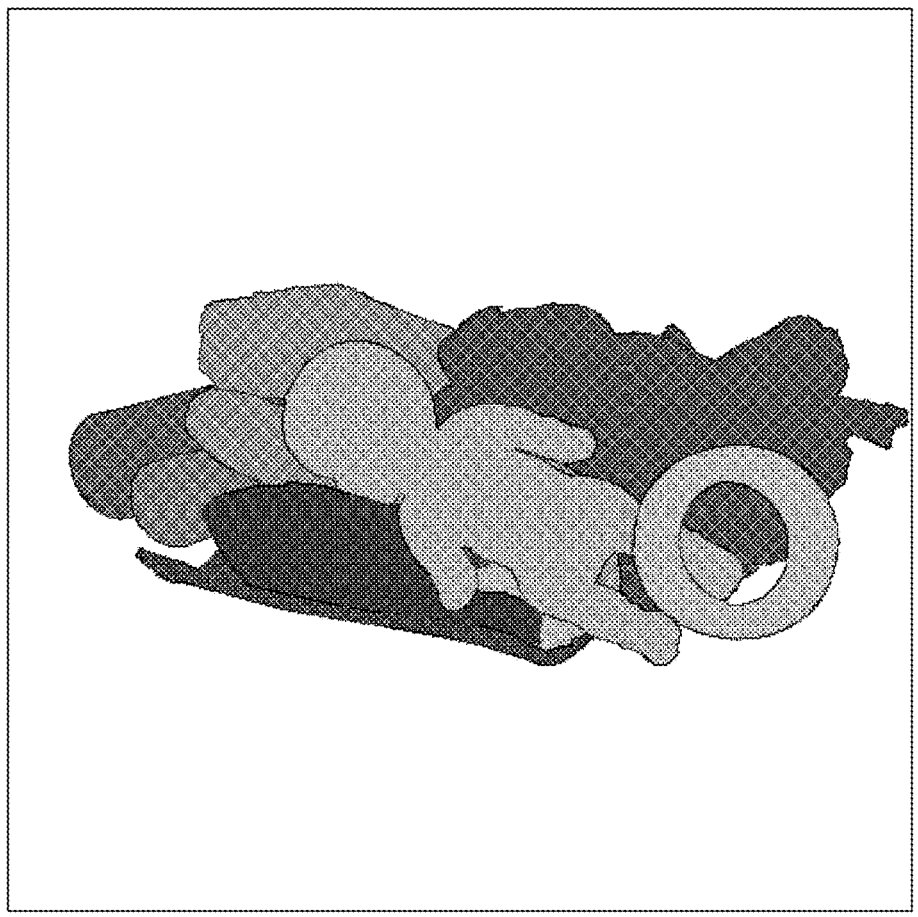
FIGS. 2A-2B illustrate an object ID map in accordance with an aspect of the present invention.
Figure 2B:
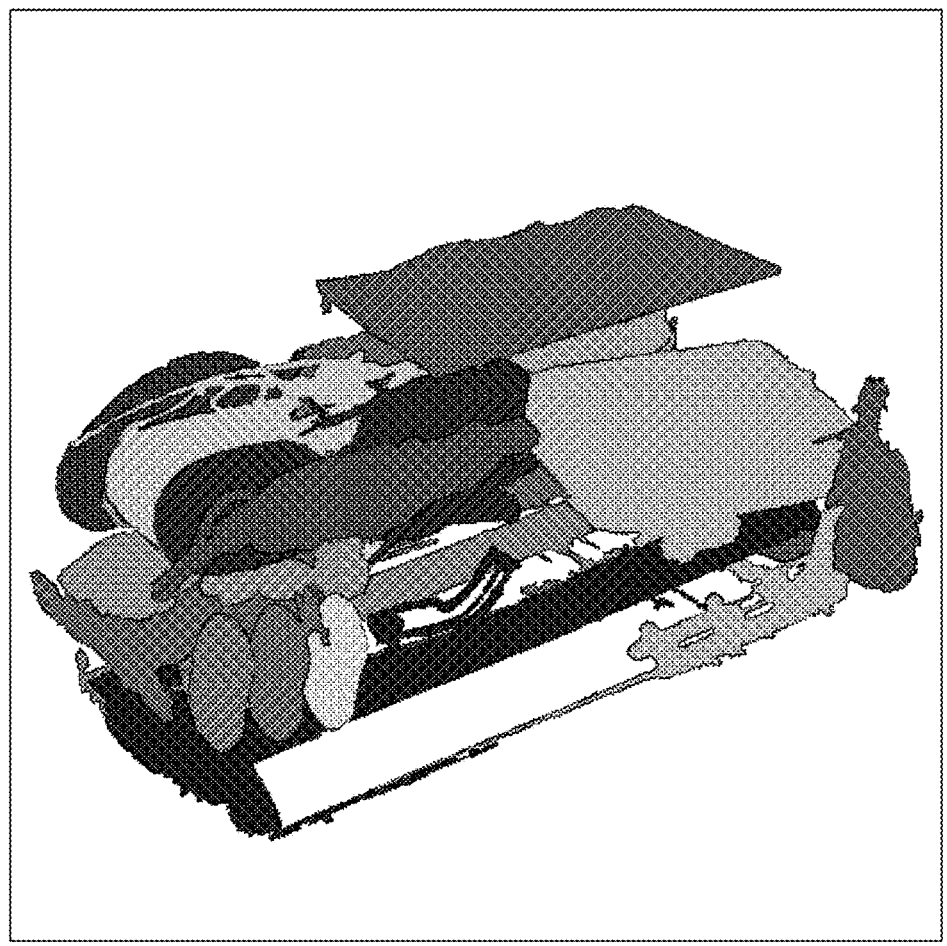
Figure 6A:
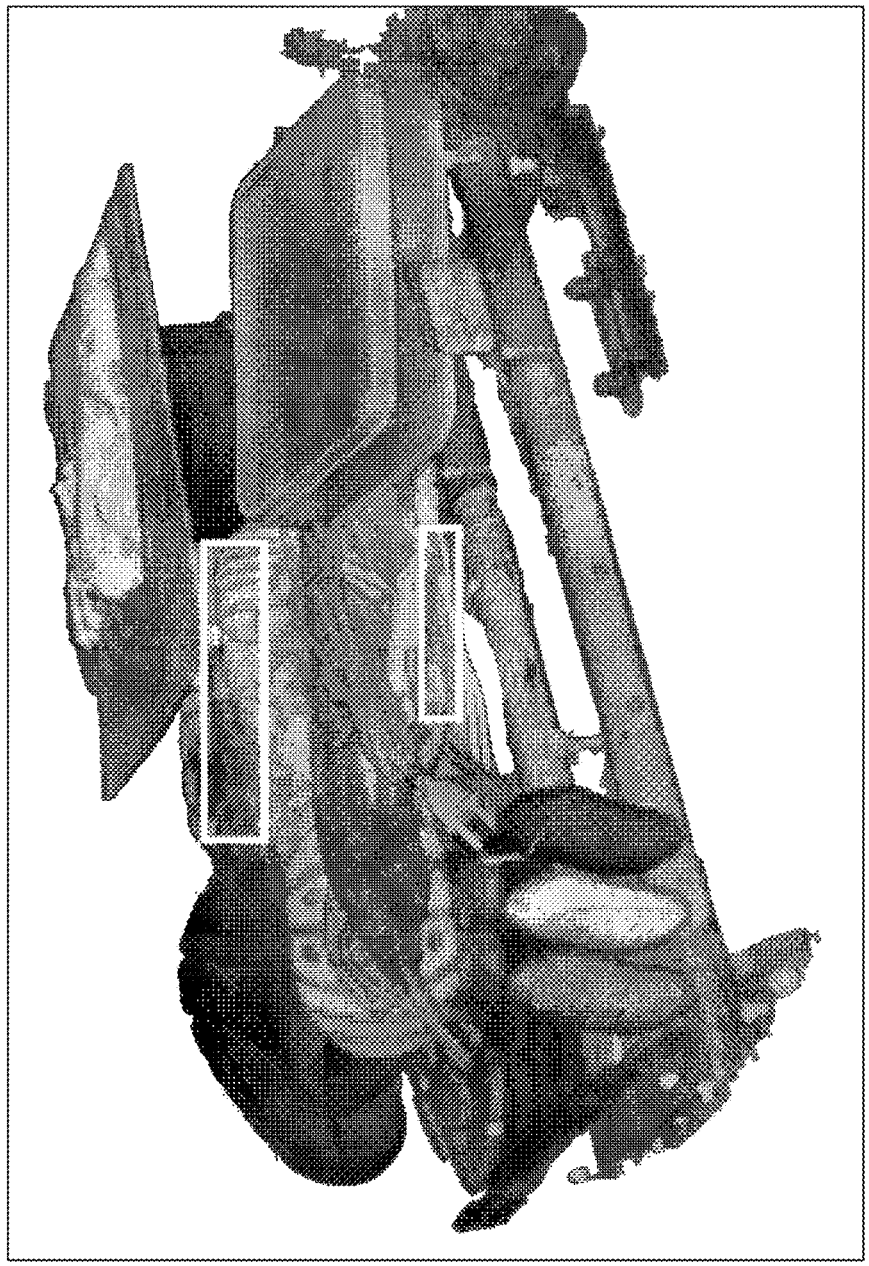
FIGS. 6A-6D illustrates luggage visualization in accordance with an aspect of the present invention.
Figure 6B:
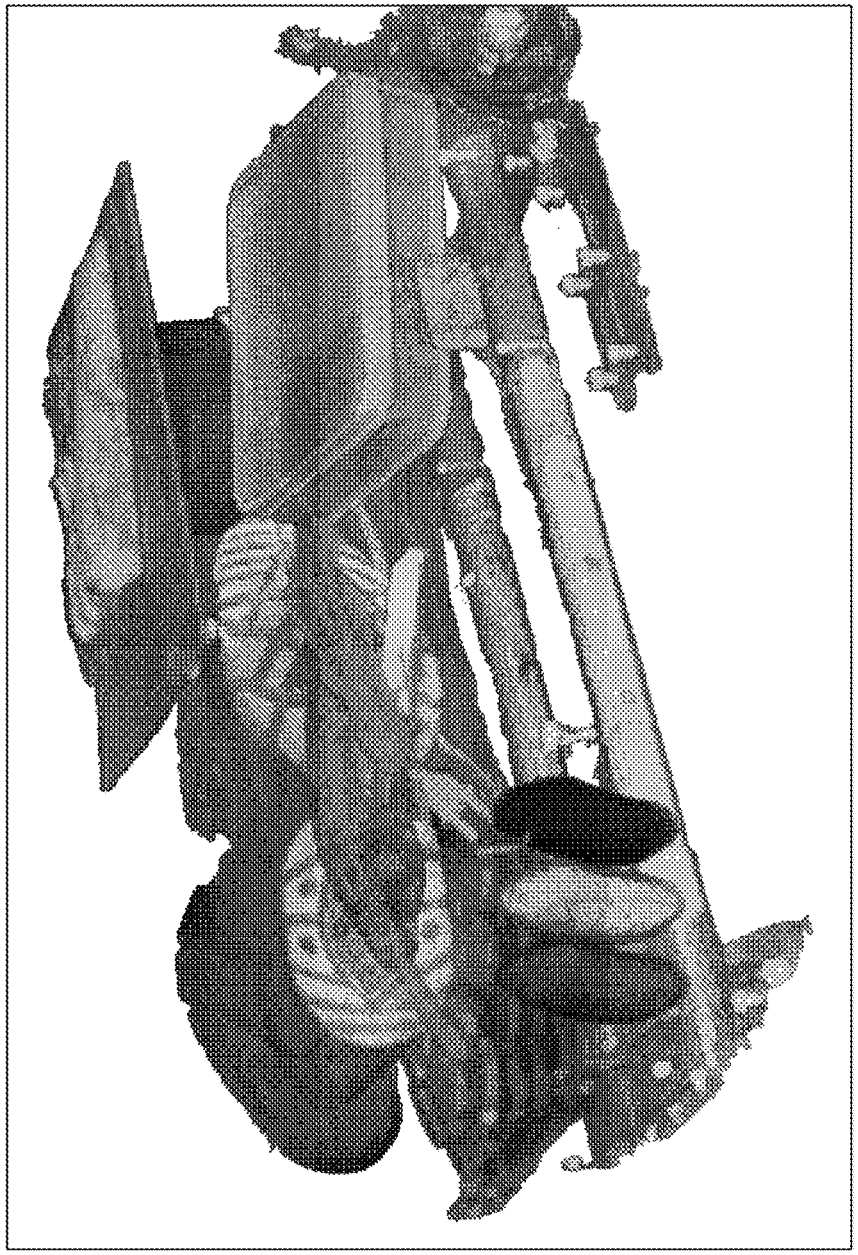
Figure 6C:
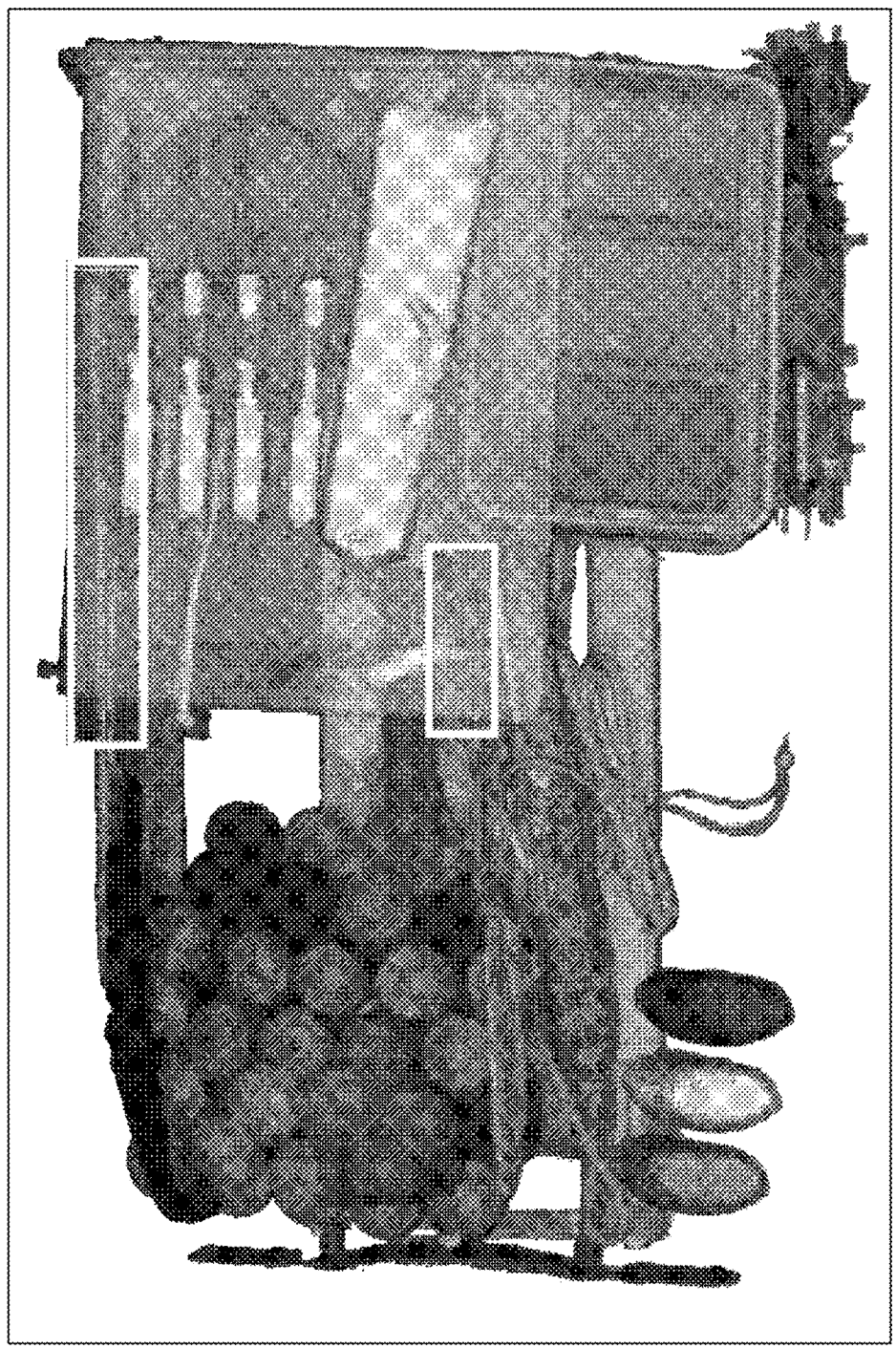
Figure 6D:
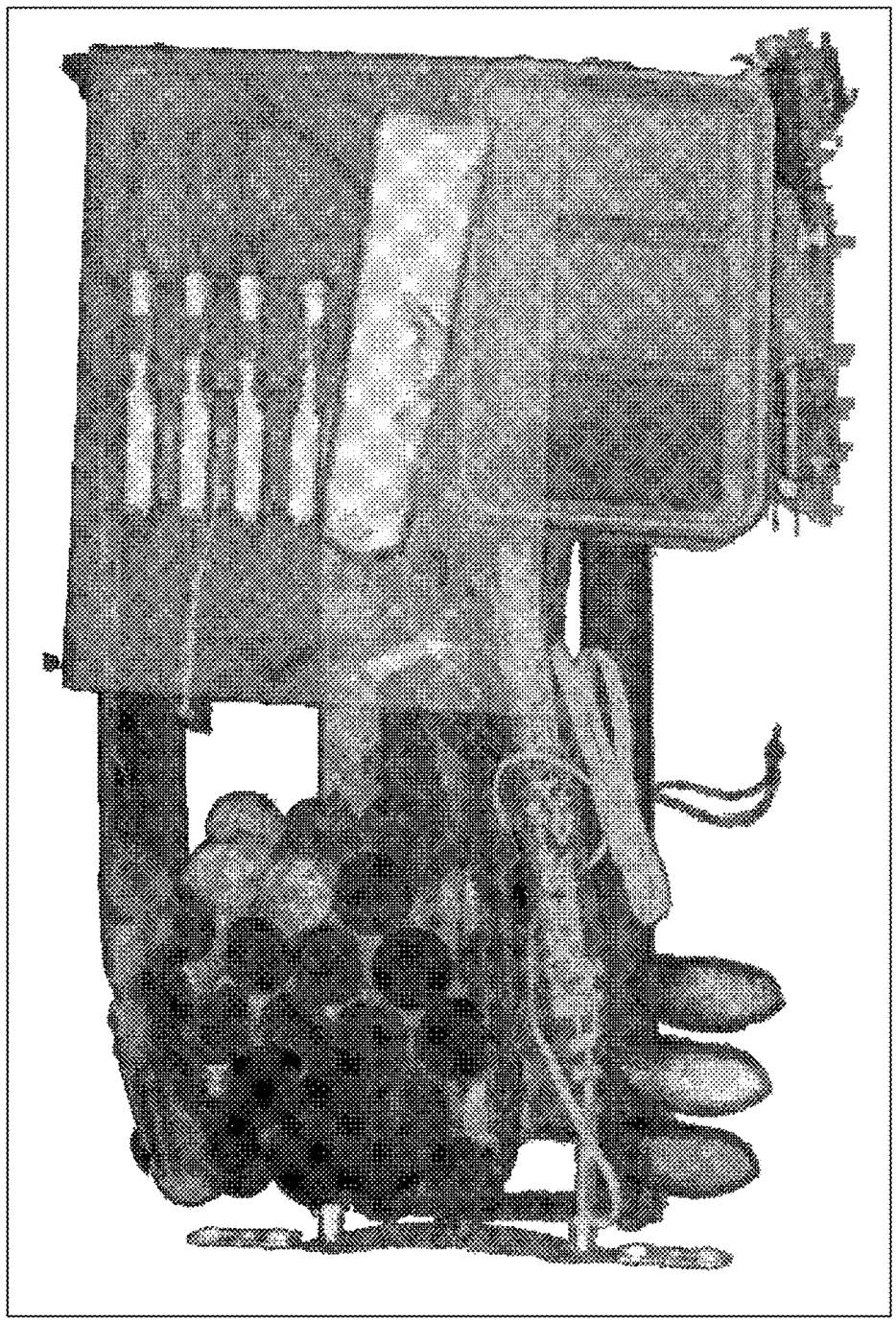

Standard volume rendering is modified to generate object ID images in which each volume sample belonging to a visible object outputs the object ID as its color, and all the samples are mapped with full opacity. FIGS. 2A and 2B show as examples two object ID maps represented in grey scale (though in actual use of aspects of the present invention these would be full color images) that are used for the scenes shown in FIG. 1 and FIG. 6 respectively. Note that the true object ID maps contain the indices of objects. Here the object IDs are visualized with their tinting colors. Each pixel of the resulting image contains the ID of the nearest object covering the pixel or the pixel is zero if no object projects onto it. Similar to depth peeling as described in "[6] EVERITT, C. 2001. Interactive order-independent transparency. NVIDIA white paper" and "[17] NAGY, Z., AND KLEIN, R. 2003. Depth-peeling for texture-based volume rendering. In Pacific Graphics, 429" multiple layers of these object IDs can be generated, by assigning zero opacity to all the objects presented in the previous layers and repeating the rendering until enough layers are generated. In FIGS. 2A and 2B the first layer of object ID maps for FIG. 2A is the luggage scene in FIG. 1 and in FIG. 2B the scene in FIG. 6B respectively. Note that the true object ID maps contain the indices of objects. In FIGS. 2A and 2B the object IDs with their tinting colors are visualized in grey scale representation.

It is declared that two objects A and B are interfering, if the following formula is true:

$$\min_{layer(pA) \leq LT \wedge layer(pB) \leq LT} (DIST(Pa, Pb)) \leq DT \quad (1)$$

where pA and pB are pixels in an image projected from the front faces of objects A and B respectively. dist(pA, pB) computes the distance between the two pixels in image space. DT is a predetermined distance threshold. layer(p) returns the layer index of pixel p. LT restricts the computation to the first LT layers.

Obviously, if all objects are opaque, only the first layer is needed. For luggage visualization, objects are typically semi-transparent while having sufficient opacities. In practice, only samples from the first two layers present useful information, and a single-layer object ID image works pretty well for most of the use cases.

An interference map is generated in accordance with an aspect of the present invention from the object ID images through a 2D filtering where formula (1) is evaluated. The output is a 2D table of which each row maps to an object ID. So is each column. Initially, every cell of the table is cleared with the value false. If two objects interfere, the corresponding cell is set to true.

The object ID images can be read back from the frame buffer into system memory and the interference detection is performed in CPU. Alternatively, if scattering is supported, it can also be done on the GPU and avoids the read back. In the present implementation, an NV_shader_buffer_load OpenGL extension is utilized to allow the writing to the object interference table from the fragment shader. Other APIs such as Cuda and OpenCL can do the same. One thing to notice is that the table only have boolean values and any cell changes at most once from false to true during the detection. It does not matter if an entry is set to true multiple times. As a result, there is no need to use any lock to synchronize reading or writing to the table.

Once the edges of interfering objects are determined, any graph coloring algorithm can be utilized to determine the minimal number of colors, C. The greedy algorithm was selected that processes vertices in decreasing order of degrees. One important difference between the color optimization as applied in accordance with an aspect of the present invention and standard graph coloring is that it is intended to fully utilize the color space, instead of minimizing the number of colors. Therefore, all the objects are divided into C clusters according to the output of the graph coloring. Then each cluster is assigned one of the evenly partitioned regions in the color space.

Figure 3:
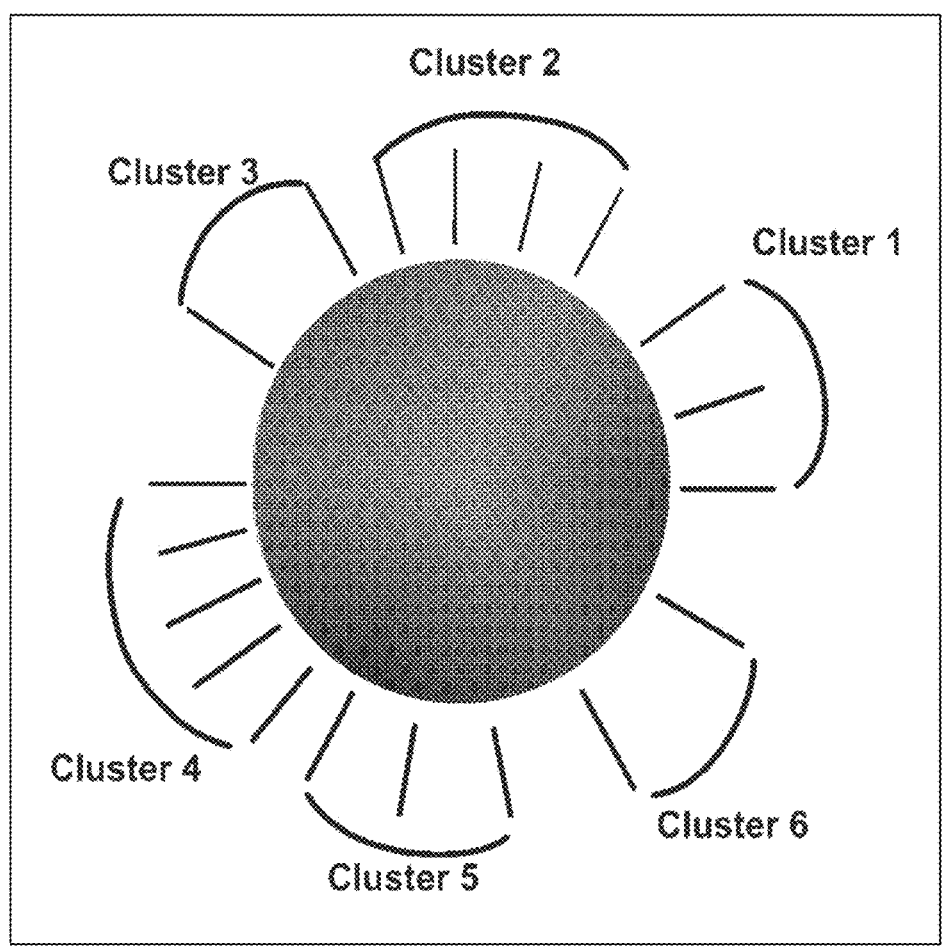
FIG. 3 illustrates color assignment in accordance with an aspect of the present invention.

To make the tinting approach more effective, the color optimization is performed in HSV space, and only a hue (H) is assigned with S and V stay at their maximal values. This reduces the color space to an 1D circle. Next, the objects in a cluster is sorted according to the number of interfering neighbors in the next cluster. The objects are then evenly distributed in the color region assigned to the cluster, with the object having the most interferences furthest away from the next cluster. FIG. 3 illustrates such an assignment where all the objects are grouped into six clusters with different number of elements. FIG. 3 is shown in grey shading but represents a color space assignment. Each object is assigned different hue with interfering objects separated to different clusters.

It is still possible that two interfering objects assigned to different clusters are adjacent in the hue space. One option is to add additional hue margin between clusters. However, with the dataset that was applied for testing, this does not present noticeable problems.

Virtual Unpacking

The goal of virtual unpacking is to visually separate individual objects without actually modifying the original volume. A typical work flow is to unpack objects one-by-one or group-by-group. The occlusion of the remaining objects reduces as the number of unpacked objects increases. Unpacked objects stay visible in the scene reminding users of the history, and can be individually inspected with standard volume rendering operations.

It is desirable to visualize the transition of objects from packed to unpacked positions, so that the context of any object can be examined, and the impact of potential false segmentation is minimized. For instance a segmentation yields 3 objects, a tube a curved pin and a grip like object. A viewer, especially a trained one, when viewing the unpacked objects, will immediately recognize that the 3 objects are a barrel a trigger and a grip that combined form a gun, especially when the relative orientation of the objects is maintained during unpacking and parts are displayed relatively close on a screen. This allows a viewer to easily recombine in his/her mind the objects to its original shape. For a similar reason, a system as provided in accordance with an aspect of the present invention also provides animated restoring or re-packing if a user wants to repeat inspecting an unpacked object in its original environment. In that case the inspector will see how the 3 objects combine into a gun. In that case the inspector may enlarge the image and view it from different points of view on the screen, for instance by rotating the image.

Unpackable Object Determination

Only unblocked objects can be unpacked. Otherwise, an object being unpacked may pass through others. To determine whether an object is unpackable along a certain direction $\vec{D}$, first an object ID image $I_{oid}$ is generated using the opposite direction of $\vec{D}$ as the viewing direction. Then another pass is performed of modified volume rendering using the same viewing direction. Both of the two rendering passes use orthogonal projection. The goal of the second pass is to compute the occlusion ratio of each object A according formula (2):

$$\frac{\Sigma_{sA \in A \wedge A \neq objectId(proj(sA))}(1)}{\Sigma_{sA \in A}(1)} \quad (2)$$

where sA is a volume sample enclosed by A, and objectId (proj(sA)) is the object ID in $I_{oid}$ where sA is projected onto the image plane.

Basically, formula 2 computes the ratio of occluded samples versus the total samples of object A. Obviously, a zero ratio indicates that A is unoccluded. Because each object can have arbitrary shape, it is possible that every object is blocked by others for a given direction. In the extreme, one object may be blocked in all the directions. When there is no object having zero occlusion ratio, the system either asks users to choose a different unpacking direction or select the object with the least occlusion ratio as unpackable.

One unpacking option is to use the up direction when a suitcase lies on its largest surface as the $\vec{D}$, which emulates the scenario of taking object out from an opened luggage. Another choice is to use the opposite of the viewing direction as the unpacking direction, which is roughly equivalent to unpacking the front-most object in the current view. Although it is different from an actual unpacking, this choice could be more useful for virtual unpacking.

For example, a user may rotate an image of a suitcase so that an interesting object is rotated to the front or at least with occlusion reduced. It is natural that the interested object be unpacked within the next few steps. As discussed further below, unpacking from the viewing direction also simplifies rendering. The description herein of an illustrative embodiment describes only performing unpacking in this direction. It is to be understood that unpacking in accordance with one or more aspects of the present invention can take place in any direction that is desired and/or selected by a user such an inspector or preprogrammed on a processor and is fully contemplated.

The occlusion ratio table of all the objects that are still packed is updated whenever the unpacking direction is changed or when all the unpackable objects determined in the previous update are unpacked. The GPU (graphics processing unit) is utilized to accelerate the process. Depending on hardware capability, two approaches are provided in accordance with different aspects of the present invention. The first approach exploits occlusion query that counts the number of fragments passed to the frame buffer.

The following pseudo-code is executed in the fragment shader:

```
firstId = Ioid [ fragmentCoord ] ;
void find1stOccluded ( )
{
    if ( idOf ( sample ) != queriedId ) discard ;
    if ( queriedId = = firstId ) discard ;
    if ( ! firstSampleOf ( queriedId ) ) discard ;
};
```

The modified volume rendering is performed N times, where N is the number of visible objects that are still unpacked. In each pass, queriedId equals to the ID of the object being queried. Only the front-most samples belonging to the object pass if queriedId is different than the corresponding value, firstId, in Ioid. Occlusion query returns the sum of occluded first-hit samples of object$_{queriedId}$. The total samples of the object can be evaluated similarly using only the first if statement of the above code. In practice, just the front face area of the bounding box of the object is used for approximation.

Each pass is optimized to only render the sub-volume defined by the bounding box of object$_{queriedId}$. But the accumulated time of tens of rendering passes may still introduce noticeable delay. Therefore, also a single pass method is provided in accordance with an aspect of the present invention taking advantage of the scattering and atomic counter capabilities of modern GPUs.

The following pseudo-code is executed for each ray in a ray-casting setup.

```
void countOccludedSamples ( )
{
    fcurrentId = -1;
    samples = 0 ;
    firstId = Ioid [ fragmentCoord ] ;
    while ( moreSamples ) {
        id = idOf ( sample ) ;
```

```
        if ( id = = firstId ) continue ;
        if ( id = = currentId ) samples ++;
        else {
            updateCounter ( currentId , samples ) ;
            currentId = id ;
            samples = 1 ;
        }
    }
    updateCounter ( currentId , samples ) ;
};
void updateCounter ( currentId , samples )
{
    if ( currentId > 0)
        atomicAdd (&counter [ currentId ] , samples ) ;
}
```

The pseudo-code counts contiguous samples belonging to an occluded object, and adds the partial sum to the counter table shared across all fragment shaders if the end of the ray is reached or the current object Id changes.

Volume Rendering

The rendering of one or more objects moving from their original packed positions in the context of others that are still packed faces the same challenge as exploded views of volume data as described in "[3] BRUCKNER, S., AND GRÖLLER, M. E. 2006. Exploded views for volume data. IEEE Transactions on Visualization and Computer Graphics 12, 5 (9), 1077-1084", multi-object or multi-modality volume rendering as described in "[2] BRUCKNER, S., AND GRÖLLER, M. E. 2005. Volumeshop: An interactive system for direct volume illustration. In Visualization, H. R. C. T. Silva, E. Gröller, Ed., 671-678" and "[1] BEYER, J., HADWIGER, M., WOLFSBERGER, S., AND BHLER, K., 2007. High-quality multimodal volume rendering for pre-operative planning of neurosurgical interventions", and multi-layer volume rendering as described in "[14] KAINZ, B., GRABNER, M., BORNIK, A., HAUSWIESNER, S., MUEHL, J., AND SCHMALSTIEG, D. 2009. Ray casting of multiple volumetric datasets with polyhedral boundaries on manycore gpus. In ACM SIGGRAPH Asia, 152:1-152:9" and "[16] LI, W. 2010. Multi-layer volume ray casting on gpu. In Volume Graphics, 5-12."

Because of the displacement of some portion of a volume, visibility order of samples cannot be inferred from their volume coordinates. The boundaries of the moving portions and the bounding box of the original volume partition the space into multiple regions. For a volume ray casting, rays are divided into segments each has different parameters from its predecessor and successor on the same ray. In the case of one object or volume portion overlaps with other non-empty part of the volume, multi-volume or fused volume rendering as described in "[12] GRIMM, S., BRUCKNER, S., KANITSAR, A., AND GRÖLLER, M. E., 2004. Flexible direct multi-volume rendering in interactive scenes, October" and "[3] BRUCKNER, S., AND GRÖLLER, M. E. 2006. Exploded views for volume data. IEEE Transactions on Visualization and Computer Graphics 12, 5 (9), 1077-1084" is required.

The fragmentation of rays introduces a lot of branches into the rendering code that severely degrades the performance. Besides, allowing one object to overlap and to pass through others is also not visually plausible for unpacking. In one embodiment of the present invention, the unpacking path is restricted to always start in the opposite of the viewing direction, thereby starting to move the object along a path towards the observer (simulating the act of grabbing an object from the luggage), and subsequently moving the object to an unpacked location (simulating the act of placing the object outside of the luggage). Note that orthogonal projection is used when determining the unpackability. For a fully unblocked object, the displacement in the opposite of the viewing direction (towards the observer) guarantees that the object being unpacked is always in front of the objects that are still packed, with the camera being in either perspective or orthogonal projection. Until the object being unpacked is completely outside the bounding box of the volume, it moves towards its unpacking location. As shown in FIG. 1, the doll first moves towards the camera as it appears larger in FIG. 1B than in FIG. 1A due to the perspective projection of the camera, then it moves in the up-right direction of the image space.

Unpacking Animation

Figure 4A:
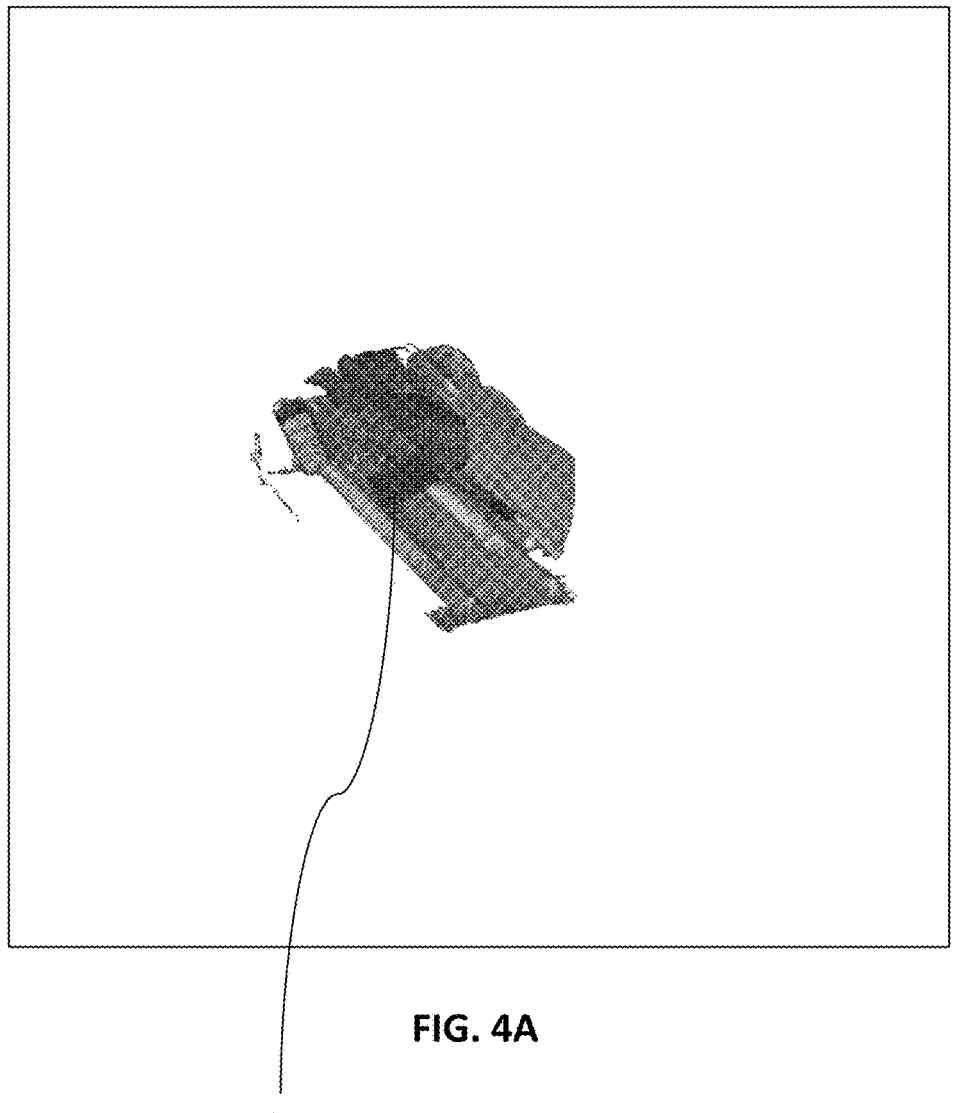
FIGS. 4A-4D illustrate virtual unpacking of an object in accordance with an aspect of the present invention.
Figure 4B:
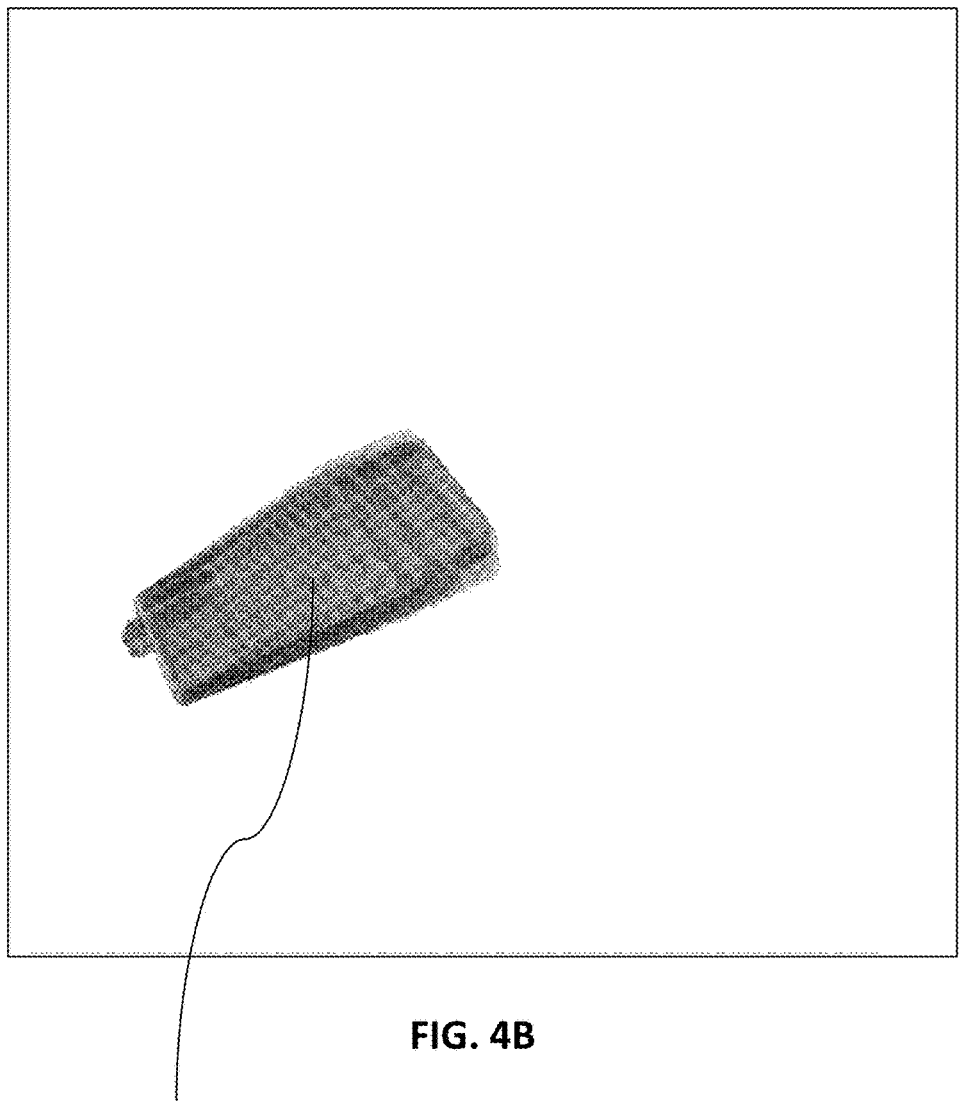
Figure 4C:
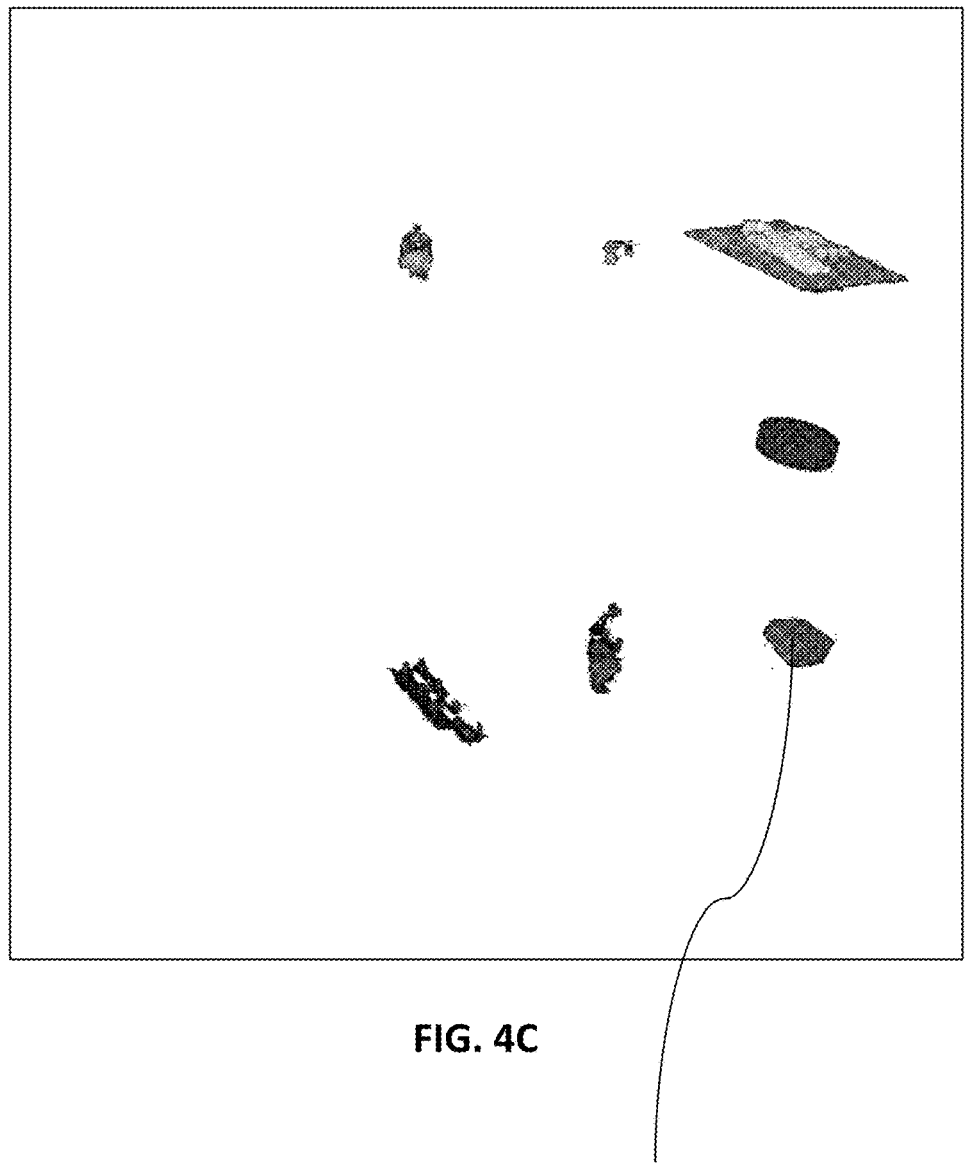
Figure 4D:
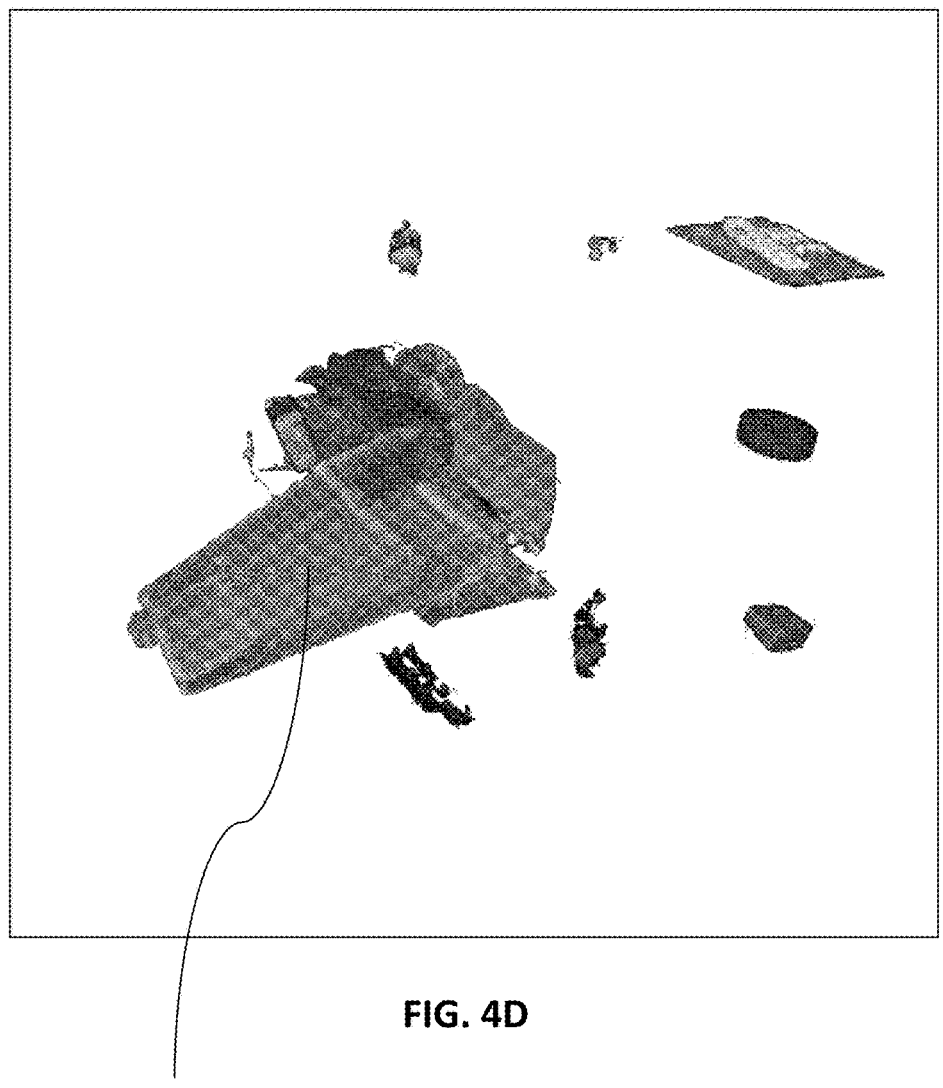

To efficiently visualize unpacking, the whole scene in accordance with an aspect of the present invention is divided into three layers, which are called rendering layers that are accessed by a processor. As shown in FIG. 4, the first layer (as illustrated in FIG. 4A) contains all the objects 401 still to be unpacked. The second layer (as illustrated in FIG. 4B) is responsible for showing the animation of unpacking of one individual object 402, as well as allowing a user to interactively inspect any unpacked object. The third layer (as illustrated in FIG. 4C) shows all the unpacked objects 403 as 3D sprites. Compositing the three layers together produces the visualization 404 in FIG. 4D.

To animate the unpacking of an object O, such as the box 402 in FIG. 4B, its tinting color are set to be zero and perform the tinted volume rendering described above, which essentially hides O in this layer. Next certain geometric transformation are continually applied, such as translation and rotation on the whole volume, and perform the tinted volume rendering multiple times onto the animation layer, but this time setting the tinting color of all the objects except O to zero. If there are multiple objects being unpacked simultaneously, the rendering to the animation layer is applied multiple times at every animation step, one for each unpacking object.

The sprite layer simply displays the 3D sprites of unpacked objects. The final image in the animation layer of an unpacking object is used to create a sprite of the object and added to the sprite layers.

The location of any volume sample v is transformed by cascaded matrices to generate a window coordinate w, for instance in accordance with:

$$w = V \times T \times M \times v \quad (3)$$

where M is the model matrix, and T specifies additional transformation. Their combination transforms from volume coordinates to world coordinates. T defines additional transformations, while view matrix V transforms from world coordinates to camera coordinates. All the three layers share the same camera.

The desired unpacked locations are given in eye coordinates as they should be independent on view directions, whereas the system changes the T to T'T to displace objects. For an object O, its unpacked displacement in volume coordinates T' is given by (4) as:

$$T' = (V \times M)^{-1}(u - V \times M \times o) \quad (4)$$

where u is the desired unpacked location in camera coordinates, and o is the offset vector of O pointing from the volume center to the center of the bounding box of O. $(\bullet)^{-1}$ computes the inverse of a matrix. Considering the offset vector o ensures the center of O is aligned with the desired unpacked location, regardless of its original position in the volume.

A sprite is visualized by putting a camera-space rectangle mapped with the sprite image centered at its desired location u. The sprites always face the camera and align their vertical edges with the up vector of the camera. In addition, the sprites also scale accordingly as the camera zooms.

Note that the image of the unpacked volume layer is cached and reused during the animation. Actually, it is not updated until an object is unpacked or restored, or an user changes the position or orientation of the volume. The transformation for the rendering of the unpacking animation layer follows a predefined path that contains a few key frames. At each key frame, a transformation composed of translation and rotation is defined.

The transformation applied to an unpacking object is simply interpolated from the adjacent two key frames. For the sprite layer, an embodiment of the system in accordance with an aspect of the present invention stores a set of sprites, instead of a big image composing all the time. The reasons for making such a decision are: 1) each object showing in a sprite usually only occupies a small portion of the view port, and distributed sparsely, as shown in FIG. 4C. Storing the sprites separately requires less memory than storing a big image covering the whole view port; 2) The system needs frequently to add new sprites, or to hide or remove existing sprites. Storing them separately facilitates such management. A user may select any sprite for inspection. In that case, the corresponding sprite is hidden, and a volume rendering of the object is created in place of the sprite, again by setting the tinting colors to zero for all the objects except O.

Users can perform standard manipulation, such as rotation, zoom, and changing transfer function, on O. When a user exits the inspection mode, the final image is used to update the sprite.

Interaction Behavior

By analyzing the typical requirements of unpacking interaction, as well as exploiting the capabilities of a system as provided herein in accordance with one or more aspects of the present invention, the system is designed to respond to user interactions in the following way:

1. Requirement for rotation and translation are considered operations to the current active object, which is determined by the position of mouse cursor when the left button is clicked. If a ray pick originated from the position hits any sprite, then the corresponding object becomes active. Otherwise, the active object is the whole volume composed of the objects that are still packed.

2. A double click of the left mouse button attempts to pick a sprite as in the previous case. If such a sprite is found, the system gets into the inspection mode, for which the volume rendering camera will automatically pan and zoom to make the active object appear in the center of the scene with comfortable zoom, in addition to forwarding all rotation and translation requests to the object.

3. Whenever the viewing direction of the packed volume changes, a computation to determine unpackable objects as described earlier herein is performed, and their IDs are put into an unpackable object queue.

4. If an unpacking requirement is received, the first one or more unpackable objects in the queue are unpacked and the process is animated as described herein earlier.

5. If a restoring requirement is received, the latest unpacked objects are added back to the head of the queue, and their transitions from unpacked location to the packed volume are animated.

6. A user zoom request is considered as an operation of the camera. Therefore all the three layers are zoomed in a synchronized fashion.

Figure 5A:
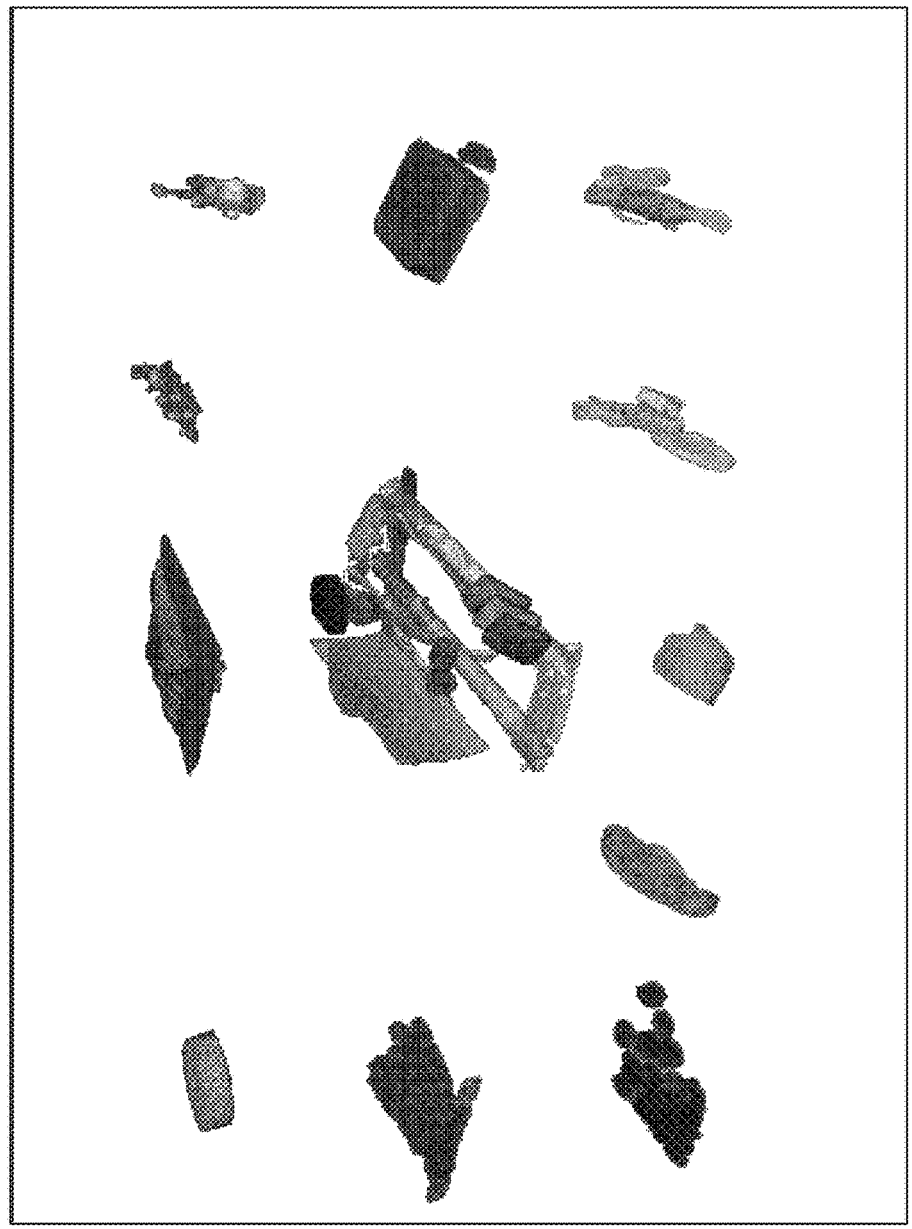
FIGS. 5A-5C illustrate unpacked objects as sprites in accordance with an aspect of the present invention.
Figure 5B:
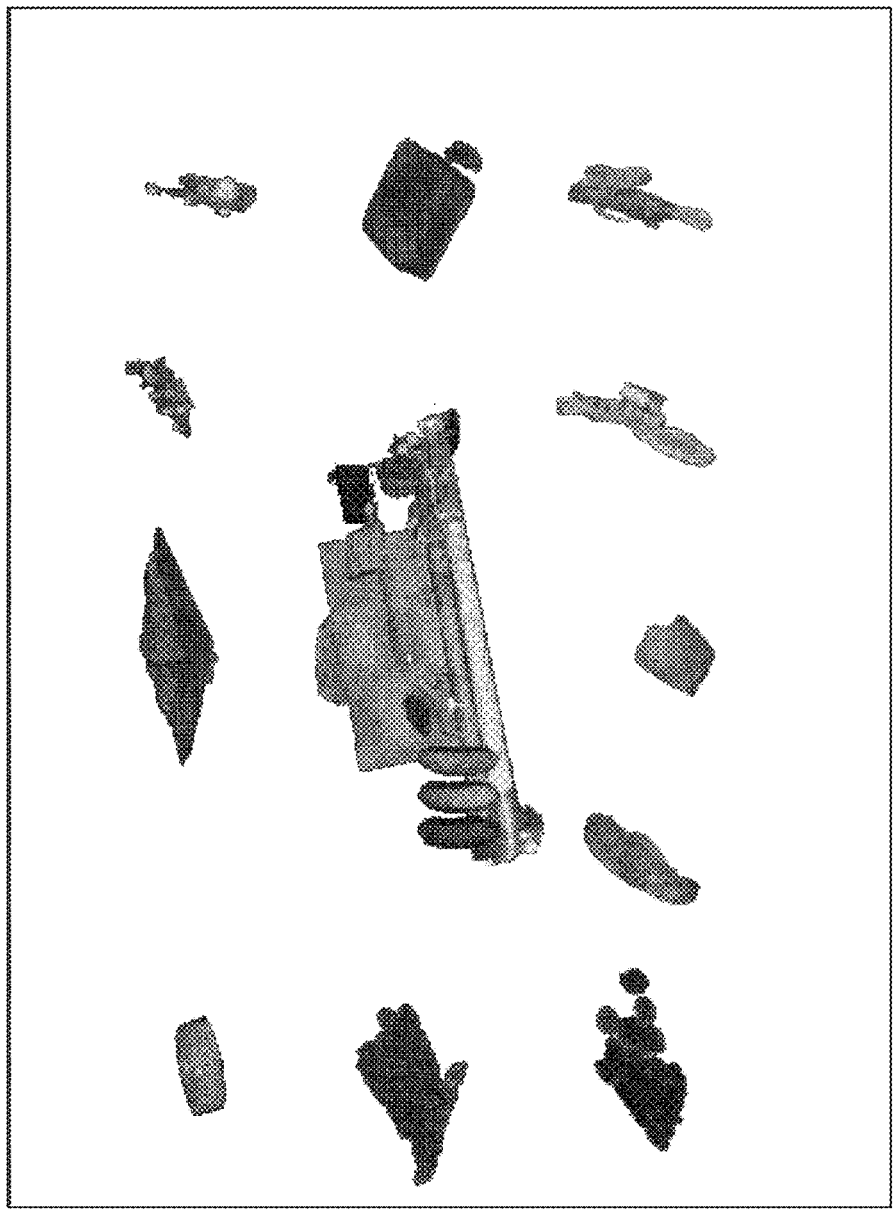

In one embodiment of a system provided in accordance with an aspect of the present invention, the sprites are not affected by any 3D rotation or translation performed on the packed volume, which is evident by comparing FIGS. 5A and 5B. Similarly, non active sprites are not affected by the manipulation on an active unpacked object either. All these transformations are applied in object space to the active object or the packed volume. In contrast, all the objects in a scene are zoomed together, as shown in FIG. 5C.

Figure 5C:
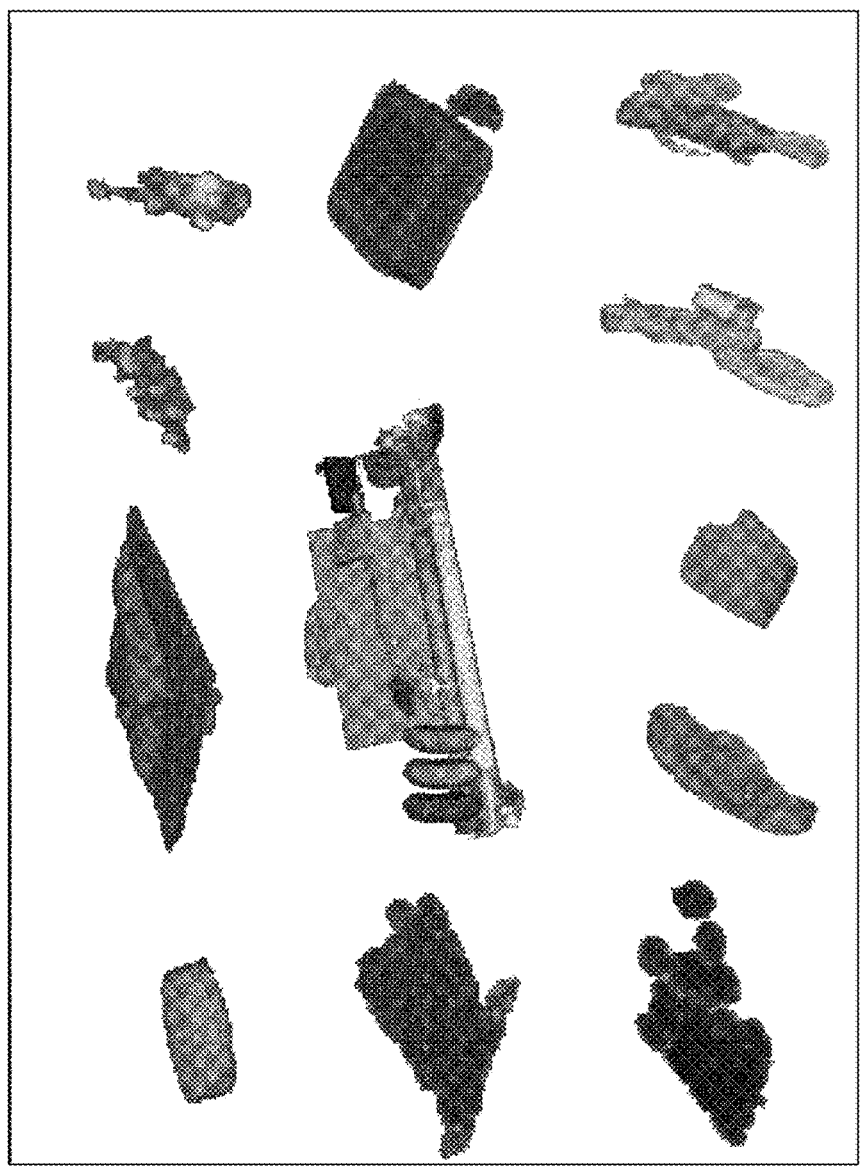

In FIGS. 5A, 5B and 5C unpacked objects are shown as 3D sprites. FIG. 5A illustrates a screen shot in the middle of unpacking FIG. 5B illustrates that sprites are invariant to the 3D rotation and translation in the volume rendering of the packed objects; FIG. 5C illustrates the response of sprites to zoom operation.

Results

An embodiment of the virtual unpacking system provided in accordance with an aspect of the present invention is implemented on a Windows-based PC. The visualization computation is mainly performed on an Nvidia Geforce GTX 480 card. The volume renderer is developed using C++ and glsl (OpenGL Shading Language). Luggage datasets are output from simulations to resemble the appearance of typical luggages going through CT scanners. Although they are not "real" luggage scans, they pose similar challenges to the segmentation and the visualization.

A typical luggage volume is of the size of 512×512×1024 with each voxel occupying 2 bytes. The dataset has significant object variations from soaps to bottled water, wax candles to boots, different clothing etc. FIGS. 6A, 6B, 6C and 6D compare the results before and after color optimization. The white rectangle in FIG. 6A highlights areas where different objects present visually identical colors, although they are different, whereas there is no such an issue in FIG. 6B.

The scene in FIGS. 6A, 6B, 6C and 6D is composed of 27 labeled objects. Rendering with such a transparency setting to a $1024^2$ view port takes about 70 ms. The animation of unpacking a single object in a view similar to FIGS. 4A, 4B, 4C and 4D takes about 50 ms for a single frame. It is faster than rendering the packed volume, because only the unpacking object is rendered and the bounding box of the object is usually significantly smaller than the full volume. Restoring animation has similar performance to unpacking. Manipulating the packed volume in a scene similar to FIGS. 5A, 5B and 5C reaches about 20 fps. This is also slightly faster than the cases in FIG. 6 because users usually would zoom out to make the unpacked objects visible in the scene, and this reduces the time for rendering the packed volume.

FIGS. 6A, 6B, 6C and 6D provide luggage visualization without (FIG. 6A) and (FIG. 6C) and with (FIG. 6B) and (FIG. 6D) color optimization. Note that in the areas highlighted by white rectangles in FIG. 6A and FIG. 6C different objects have indistinguishable color hues. In contrast, FIG. 6B and FIG. 6D do not have this issue.

Figure 7:
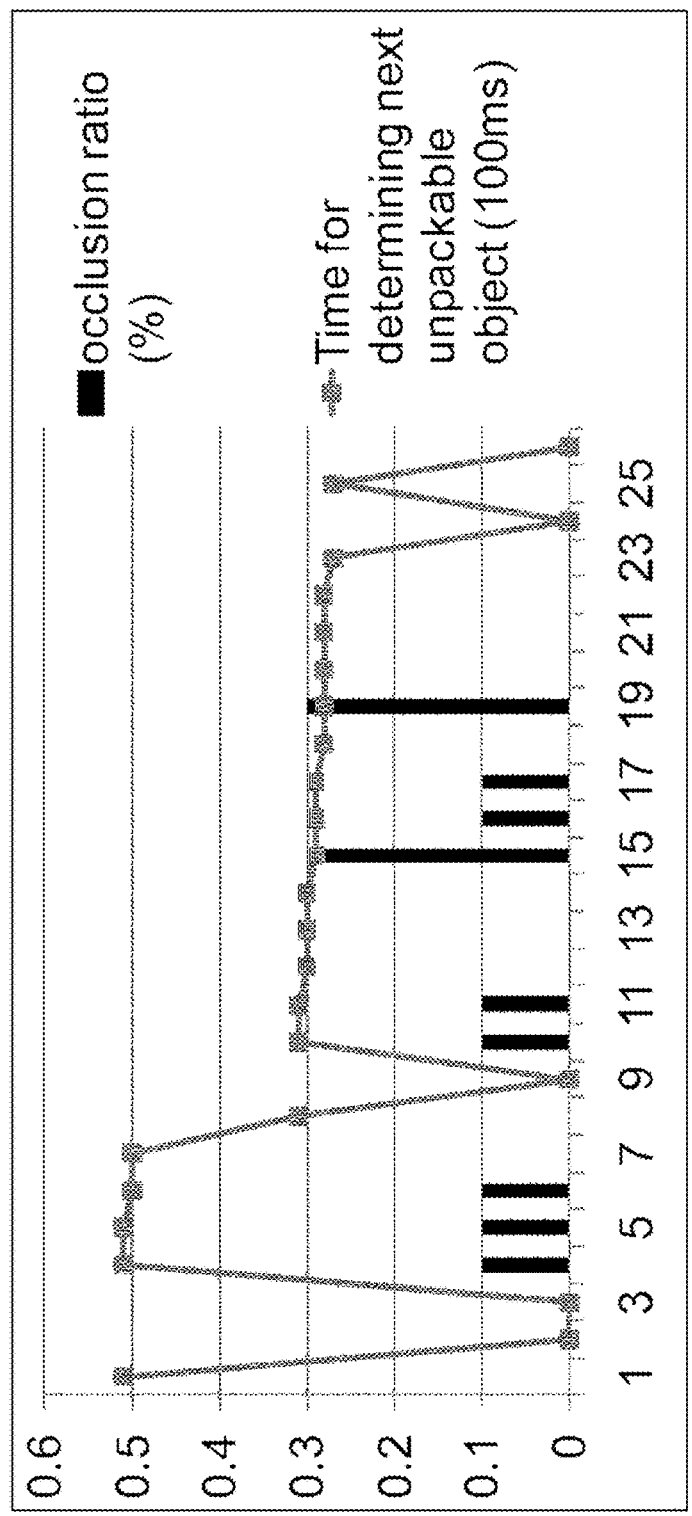
FIGS. 7 and 8 illustrate a performance of aspects of the present invention.

FIG. 7 illustrates the data of unpackable object determination during a serial process of unpacking. The multi-pass occlusion query approach was utilized. Only one object is unpacked at each step. The X axis is the index of the unpacking step. The two series show the occlusion ratio in percentage of the objects being unpacked and the time (in 100 milliseconds) for determining unpackable objects at each unpacking step. There are zeros for the time series as the previous step finds more than one unpackable object, and there is no need to run the query for the steps following immediately. Excluding those zeros, the time generally decreases monotonically, because the number of packed objects and the query passes decrease as the unpacking proceeds.

Even at the beginning of the unpacking, where the system performs the query 26 times, the overall time is just slightly more than 50 ms, which is about the time for a full quality volume rendering with the same viewing parameters. This is because the query pass for any object is restricted to the bounding box of the object, which is usually much smaller than that of the whole volume. Moreover, a querying ray terminates after reaching the first sample of the object. Whereas for a scene with a lot of transparency as in FIG. 6, a ray travels a much longer distance. The single pass approach for determining unpackable object requires the sampling of non-empty volume, which is similar to that of rendering a mostly transparent volume. Therefore, the single pass method can be slower than the multi-pass approach. Note that in FIG. 7 there are non-zero values at some steps, which means that no object is fully unblocked, although the ratio is only 0.3% at most.

Figure 8:
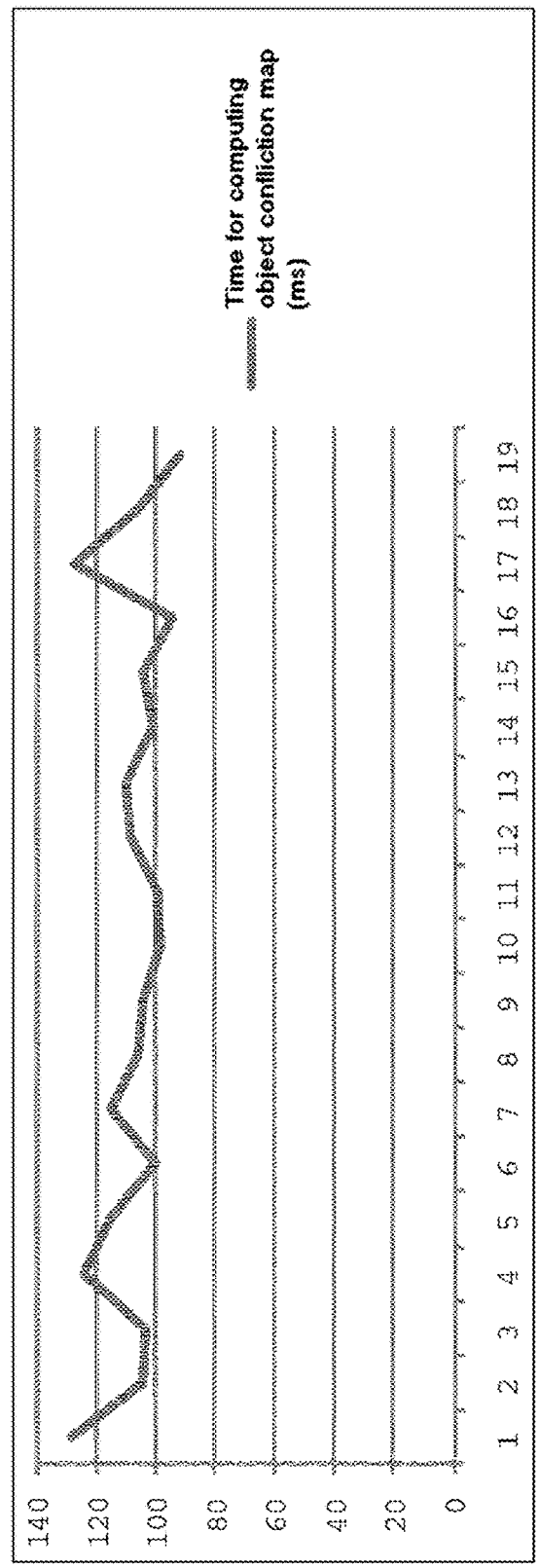

FIG. 8 presents the time for computing a single layer interference map of objects that is used for color optimization through an unpacking process. For timing purpose, color optimization is applied after the unpacking of every object, which is obviously unnecessary in practice. The average time is about 110 ms, that includes the rendering of an image of object IDs kid, the read back of kid from GPU to system memory, and the evaluation of formula (1).

Figure 9:
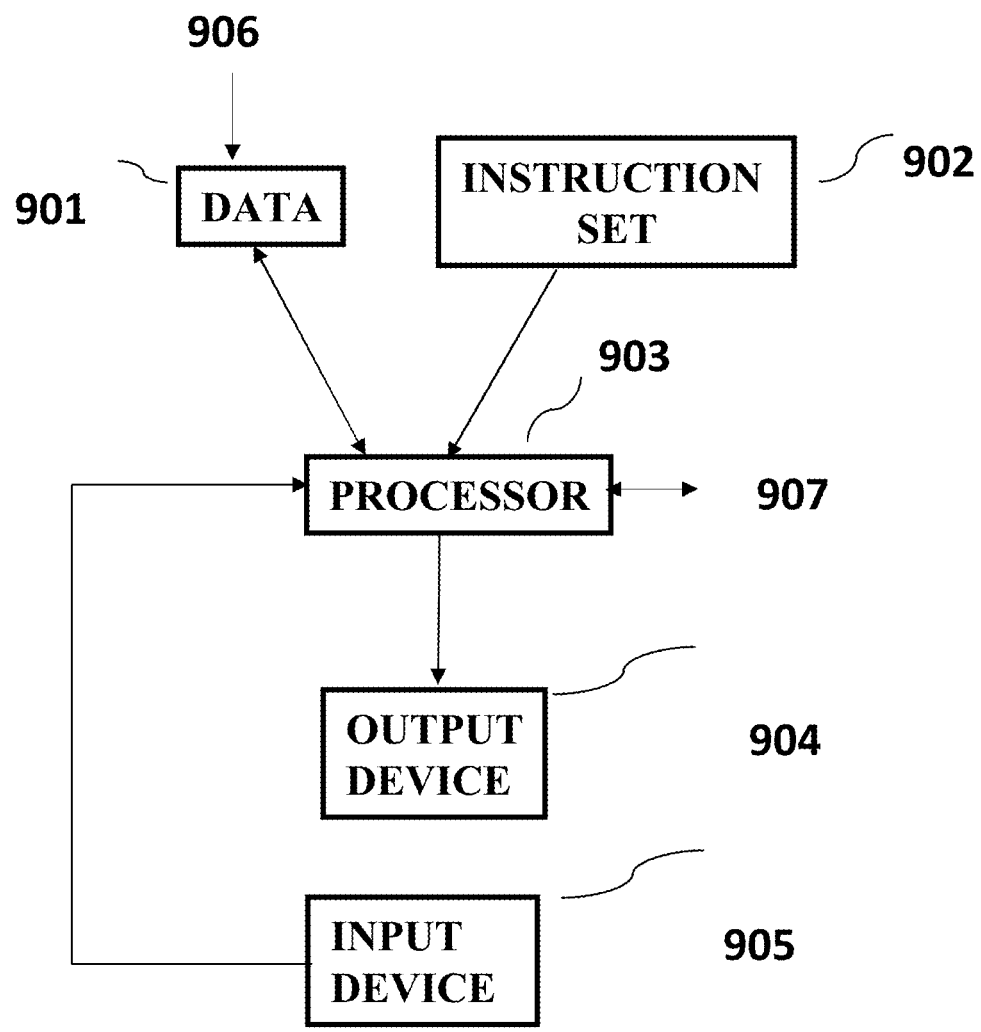
FIG. 9 illustrates a processor based system or computer enabled to execute instructions to perform the unpacking methods provided in accordance with various aspects of the present invention.

The methods as provided herein are, in one embodiment of the present invention, implemented on a system or a computer device. Thus, steps described herein are implemented on a processor, as shown in FIG. 9. A system illustrated in FIG. 9 and as provided herein is enabled for receiving, processing and generating data. The system is provided with data that can be stored on a memory 901. Data may be obtained from a scanner such as a 3D CT scanner or from any other data relevant source. Data may be provided on an input 906. Such data may be image data or any other data that is helpful in an unpacking system.

The processor is also provided or programmed with an instruction set or program executing the methods of the present invention that is stored on a memory 902 and is provided to the processor 903, which executes the instructions of 902 to process the data from 901. Data, such as image data or any other data provided by the processor can be outputted on an output device 904, which may be a display to display images or data related to luggage unpacking or a data storage device. The processor also has a communication channel 907 to receive external data from a communication device and to transmit data to an external device. The system in one embodiment of the present invention has an input device 905, which may include a keyboard, a mouse, a pointing device, or any other device that can generate data to be provided to processor 903.

The processor can be dedicated or application specific hardware or circuitry. However, the processor can also be a general CPU or any other computing device that can execute the instructions of 902. Accordingly, the system as illustrated in FIG. 9 provides a system for processing data resulting from a scanner or any other relevant data source and is enabled to execute the steps of the methods as provided herein as one or more aspects of the present invention.

It is to be understood that the present invention may be implemented in various forms of hardware, software, firmware, special purpose processors, or a combination thereof. In one embodiment, the present invention may be implemented in software as an application program tangibly embodied on a program storage device. The application program may be uploaded to, and executed by, a machine comprising any suitable architecture.

It is to be further understood that, because some of the constituent system components and method steps depicted in the accompanying figures may be implemented in software, the actual connections between the system components (or the process steps) may differ depending upon the manner in which the present invention is programmed. Given the teachings of the present invention provided herein, one of ordinary skill in the related art will be able to contemplate these and similar implementations or configurations of the present invention.

Methods and systems have been provided herein for luggage visualization where any object is clearly distinguishable from its neighbors. It supports virtual unpacking by visually moving any object away from its original pose. To achieve these, a volume segmentation guided by a confidence measure is first applied that recursively splits connected regions until semantically meaningful objects are obtained, and a label volume whose voxels specifying the object IDs is generated. The original luggage dataset and the label volume are visualized by volume rendering. Through an automatic coloring algorithm, any pair of objects whose projections are adjacent in an image are assigned distinct hues that are modulated onto a transfer function to both reduce rendering cost as well as to improve the smoothness across object boundaries. A layered framework has been provided to efficiently render a scene mixed with packed luggage, animated unpacking objects, and already unpacked objects put aside for further inspection. The system in one embodiment of the present invention uses GPU to quickly select unpackable objects that are not blocked by others to make the unpacking plausible.

To further illustrate various aspects of the present invention a series of diagrams is provided. Some of the objects of FIG. 1 have been highlighted in FIG. 10 by tracing the contours. The dashed line indicates an object that is obscured by a semi-transparent object. Lack of a contour indicates that an obscuring object is fully opaque. Clearly the doll 1001 is semi-transparent while the doughnut ring 1003 is opaque. As discussed above, unpacking will take place in a certain order, preferably in an order of visibility or occlusion in an unpacking direction towards the camera.

Figure 10:
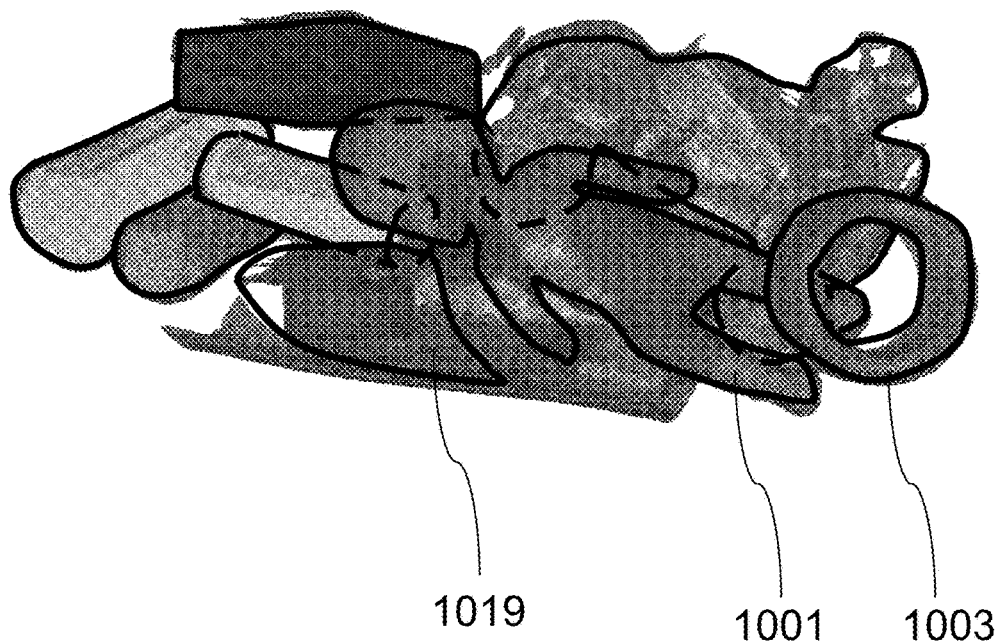
FIGS. 10 and 11 illustrate unpacking by showing contours of objects.
Figure 11:
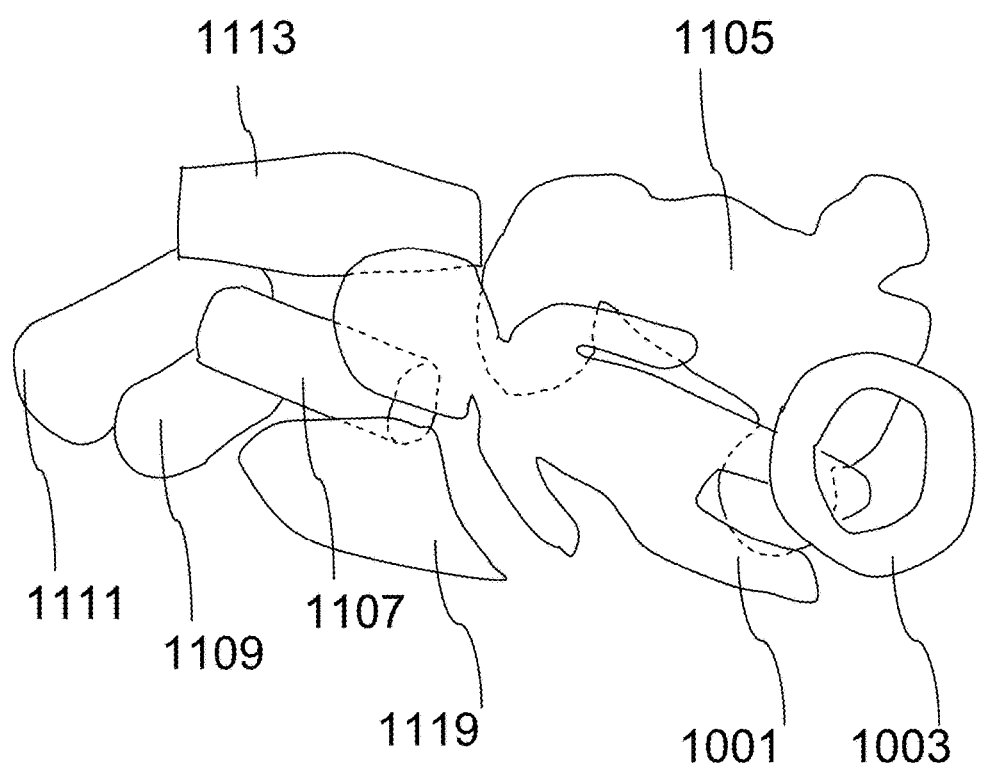

FIG. 11 further illustrates FIG. 10 by only showing traced contours. It shows the contours of objects 1101 (the doll), 1103 (the ring doughnut), 1105, 1107, 1109, 1111, 1113 and 1119. The objects are volumes generated by segmentation from a 3D volumetric image. An order or layer of visibility in the direction towards the camera also called a direction opposite to the viewing direction. Some objects are obscured or occluded by other objects. The first object closest to the camera is the doughnut ring. The next object to be unpacked is the doll 1101. One can see underlying objects 1105, 1107 and 1113 through the semi-transparent doll 1101.

It is noted that transparency of an object in a rendering is system choice which can be pre-set or selected as an aspect of the present invention. The opaqueness of a rendered object illustrates how an object obscures an underlying object in a camera view. Rendering an object as opaque or (semi-) transparent can be applied to assist an inspector to view objects that are being unpacked. It should be clear that such transparency of a rendered object in an image does not mean that the actual object is transparent.

Object 1109 obscures part of object 1111 and object 1113 also partially obscures 1111. Furthermore, object 1107 partially obscures 1109.

The unpacking of the objects occurs in the order of visibility or occlusion in such a manner that an object is not unpacked through another object. The unpacking takes place in order of visibility depending on the camera viewing direction as described earlier herein, rather than creating an instant exploded view, which may create a loss of context between objects, especially if objects are segmented incorrectly. Objects that do not occlude other objects in a certain camera view are unpacked before objects that are occluded in the camera view. If no un-occluded object exist, the processor in one embodiment of the present invention chooses an object based on a measure of occlusion ratio.

Figure 12:
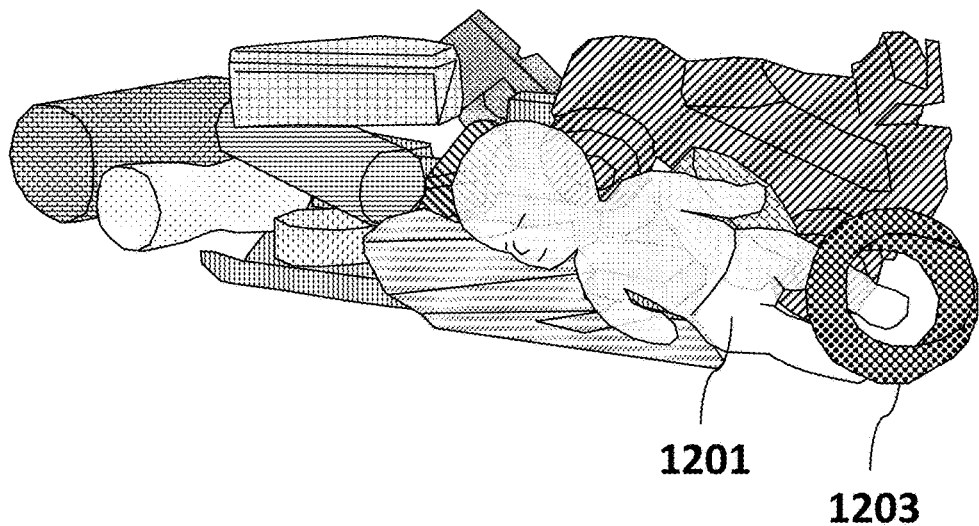
FIGS. 12-16 illustrate in diagram an unpacking of a plurality of objects in accordance with one or more aspects of the present invention.

FIGS. 12-16 illustrate steps of unpacking. FIG. 12 illustrates images of a plurality of objects wherein object 1203 is closest to the point of view and is opaque and object 1201 is behind it. Other objects are not numbered but are indicated by their patterns. An order of visibility can be determined by applying steps as provided earlier. The patterns illustrate the order of visibility and the complexity thereof.

Figure 13:
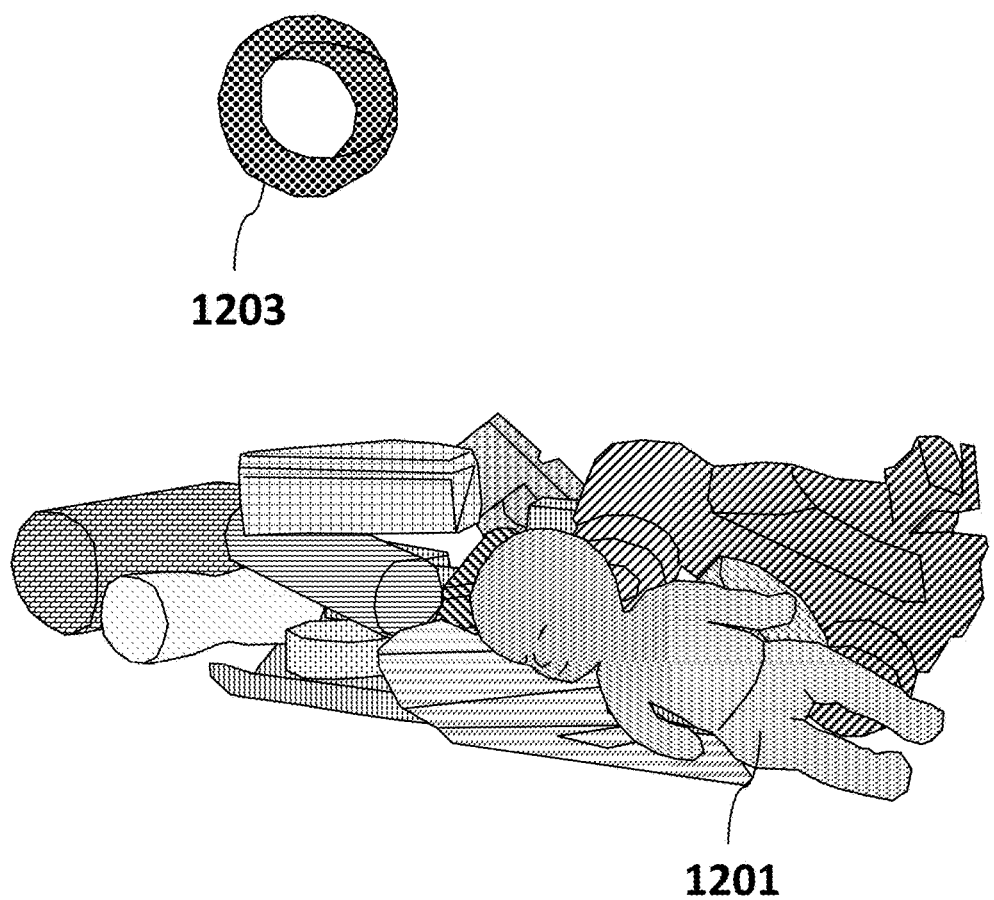
Figure 14:
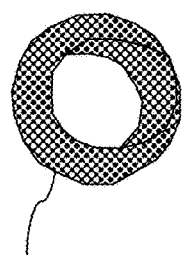
Figure 14:
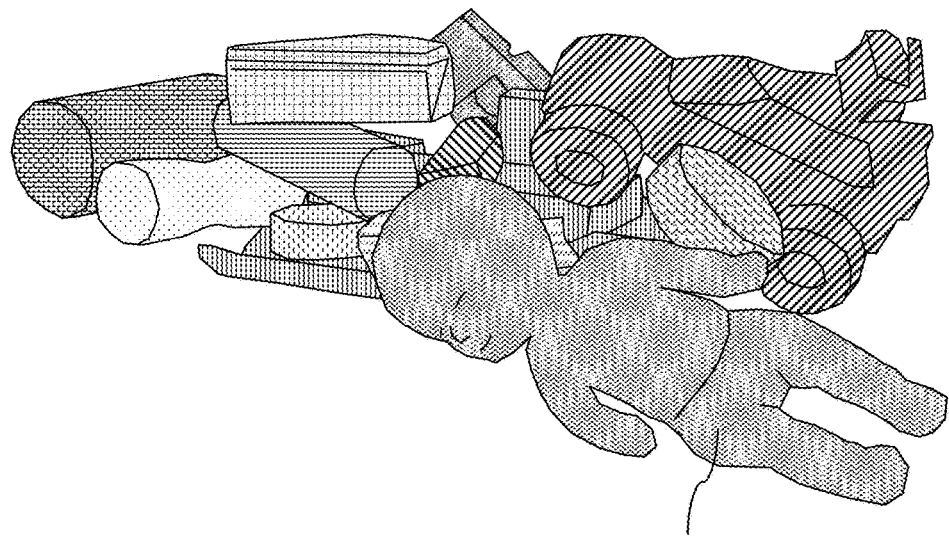
Figure 15:
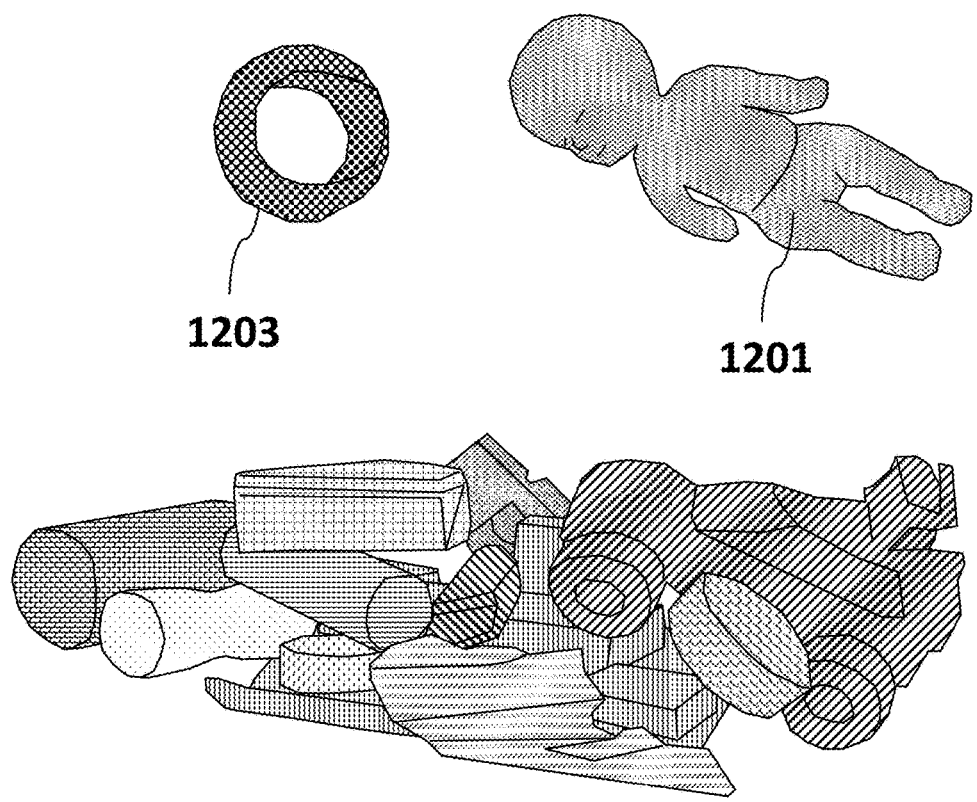

In FIG. 13 object 1203 is unpacked and moved outside the still packed objects. The next object to be unpacked is 1201 as illustrated in FIG. 14. Object 1201 is moved towards the camera in FIG. 14. and appears to have increased in size. In FIG. 15 object 1201 has been placed as an unpacked object outside the remaining packed objects.

Figure 16:
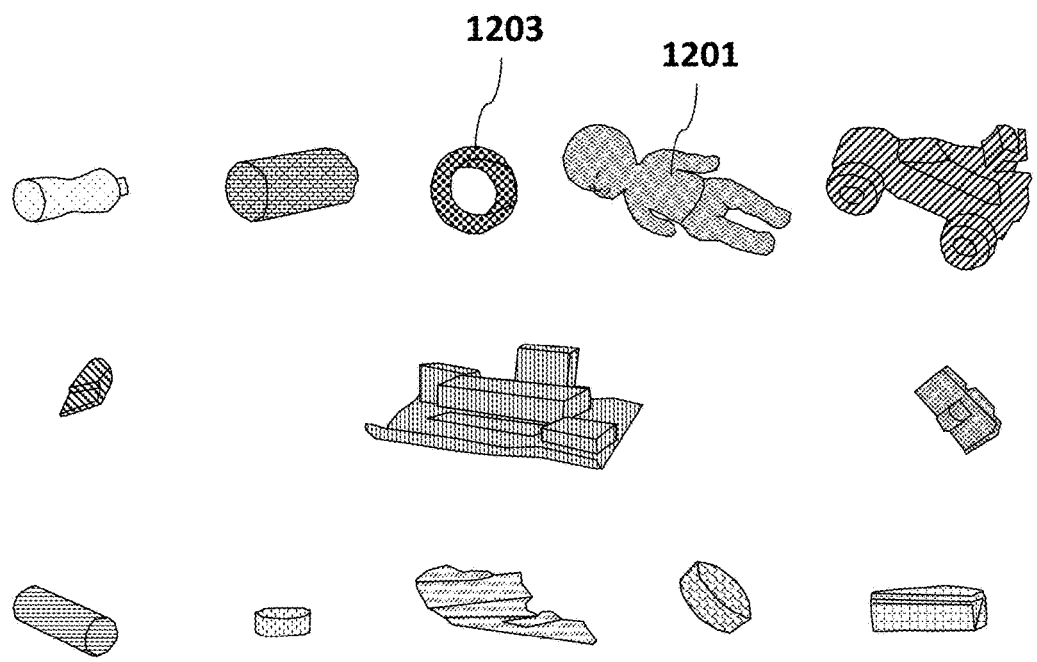

The processor continues to unpack the objects in order of visibility. The unpacked objects are arranged in such a way that their orientation remains the same and they remain in unpacked state in a position close to objects that were close in a packed state. This allows to maintain at least a positional context between the unpacked objects. The complete set of unpacked objects is illustrated in FIG. 16.

Figure 17:
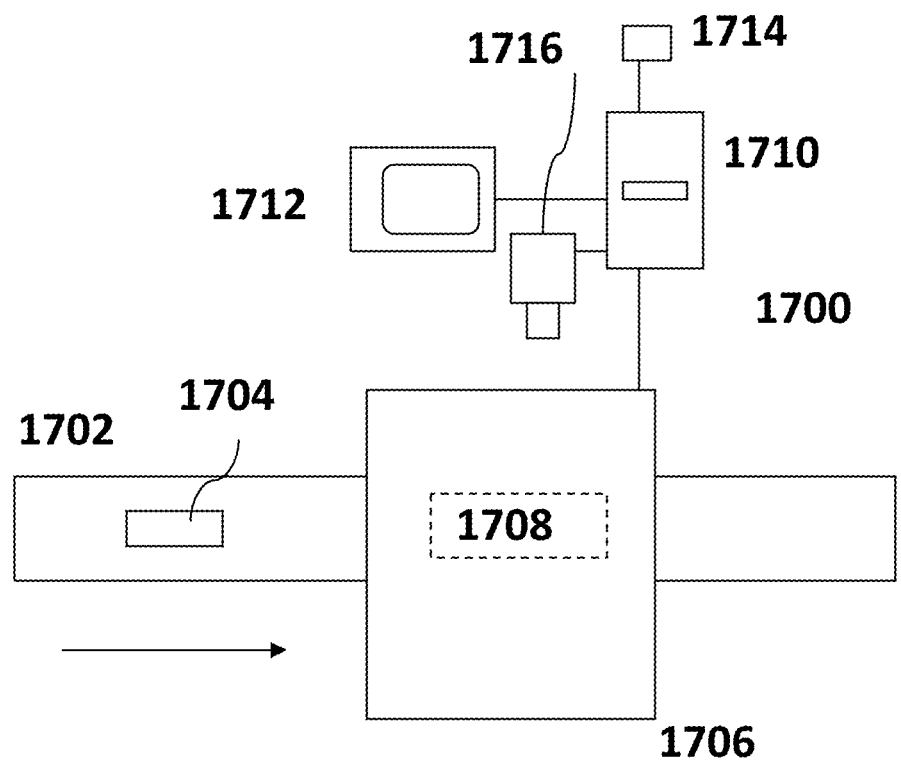
FIG. 17 illustrates a luggage inspection system in accordance with one or more aspects of the present invention.

FIG. 17 illustrates in diagram a complete inspection system 1700 for luggage using methods for unpacking as disclosed herein. The system 1700 has a transport band system 1702 to receive and transport luggage such as briefcases, suitcases, duffels and the like such as suitcases 1704 and 1708 to be placed inside a 3D image scanner 1706 such as a CT scanner. Piece of luggage 1708 is inside scanner 1708 and transport band 1702 is stopped to let the scanner 1706 scan 1708 inside the scanner. The scanner 1706 generates 3D image data that is processed by processor based computer 1710 in accordance with methods provided herein. A preferred viewing direction is pre-programmed in the computer 1710 or is selected by an inspector for instance with an input device 1714 which may be a mouse.

A sequence of unpacking images and images of the unpacked objects inside the piece of luggage 1708 is displayed on a computer display 1712. The inspector may provide instructions, for instance via input device 1714 to change a viewing direction or to reverse an unpacking into an animated re-packing of the objects or to inspect one or more of the images of the objects in greater detail, for instance by zooming in to an image. Once the inspection is completed the inspector may either order the luggage 1708 to be taken and opened for further inspection. The inspector may also declare the luggage 1708 of no interest and move the transport band to place next luggage item 1704 inside the scanner 1708 for virtual unpacking. The computer and viewing system do not have to be located near the scanner, but can be located anywhere as long there is access to the scanner data. Furthermore, a connection is provided from the computer to the transport band or personnel at the transport band to remove luggage of interest or to instruct the transport band to move. In addition a camera 1714 connected to for instance the computer is provided to provide additional information about the luggage and the scene of the luggage to the inspector or for the system to recognize if a piece of luggage is on the transport band.

The objects or images of the unpacked objects in one embodiment of the present invention are stored in a memory as individual sprites. A sprite can be retrieved individually from memory and displayed on a display individually, for instance for inspection. Sprites also allows for the plurality of objects to be re-packed as the processor will store and have access to the order of visibility and the order of unpacking. The processor can thus repack the objects in a reverse order compared to the unpacking.

In one embodiment of the present invention the virtual unpacking on a display takes place in at least a direction related to viewing direction of a virtual camera observing (and recording) the unpacking, which is the viewing direction of a viewer watching the unpacking on for instance a computer screen. The unpacking in one embodiment of the present invention takes place in a direction opposite to the viewing direction or towards the viewer. This conforms with a natural experience of unpacking a suitcase where items are generally lifted outside the suitcase by a person towards the person, before it is placed to the side of the suitcase, for instance.

In accordance with a further aspect of the present invention objects are thus virtually unpacked automatically in an order of visibility by moving an object first toward the camera (or viewer) and then placed on a spot on the screen outside the collection of remaining packed objects. Preferably, objects that are being unpacked are placed on a trajectory or curve to their place outside the suitcase, as to make the virtual unpacking as natural as possible. It is to be understood that different embodiments are possible and are fully contemplated. For instance, an object that is being unpacked can be virtually moved towards the viewer. It may be held in place, perhaps blocking the view to the other objects, for inspection for a certain period and then moved to its place outside the suitcase image. It may be moved smoothly to its spot. It may also disappear from its current spot and suddenly appear on its designated spot.

In one embodiment of the present invention, one may provide an unpacking direction that is not opposite the viewing direction. For instance one may select an unpacking direction that is perpendicular to the viewing direction, or any other direction that is deemed useful. In that case an object is first moved into the selected unpacking direction and then moved to its required spot.

In one embodiment of the present invention an unpacking direction is selected that is related to a viewing direction. In another embodiment of the present invention an unpacking direction is selected relative to dimensions of the luggage. For instance the unpacking direction may be perpendicular to the largest surface of a suitcase.

In one embodiment of the present invention the virtual unpacking is completely automatic and no human intervention is required. No marking of objects is required. All steps are performed by the processor the moment the volumetric data of the packed objects are available. In a further embodiment of the present invention human intervention is allowed to stop or accelerate unpacking to remove certain objects from view or to select an object or a layer of objects for unpacking. For instance, an inspector may render objects in a segmented but still packed state as transparent if it is believed that an object of interest is located between layers of other objects. The inspector may also remove obscuring layers of objects by making them 100% transparent to focus on unpacking of one or more layers of interest.

The following references provide background information generally related to the present invention and are hereby incorporated by reference: [[1] BEYER, J., HADWIGER, M., WOLFSBERGER, S., AND BHLER, K., 2007. High-quality multimodal volume rendering for preoperative planning of neurosurgical interventions; [2] BRUCKNER, S., AND GRÖLLER, M. E. 2005. Volumeshop: An interactive system for direct volume illustration. In Visualization, H. R. C. T. Silva, E. Gröller, Ed., 671-678; [3] BRUCKNER, S., AND GRÖLLER, M. E. 2006. Exploded views for volume data. IEEE Transactions on Visualization and Computer Graphics 12, 5 (9), 1077-1084; [4] CALLAHAN, S., COMBA, J., SHIRLEY, P., AND SILVA, C. 2005. Interactive rendering of large unstructured grids using dynamic level-of-detail. In IEEE Visualization, 199-206; [5] CHAN, M.-Y., WU, Y., MAK, W.-H., CHEN, W., AND QU, H. 2009. Perception-based transparency optimization for direct volume rendering. IEEE Transactions on Visualization and Computer Graphics 15, 6 (November), 1283-1290; [6] EVERITT, C. 2001. Interactive order-independent transparency. NVIDIA white paper; [7] GOVINDARAJU, N. K., REDON, S., LIN, M. C., AND MANOCHA, D. 2003. Cullide: interactive collision detection between complex models in large environments using graphics hardware. In Graphics hardware, 25-32; [8] GOVINDARAJU, N. K., HENSON, M., LIN, M. C., AND MANOCHA, D. 2005. Interactive visibility ordering and transparency computations among geometric primitives in complex environments. In Interactive 3D Graphics and Games, 49-56; [9] GRADY, L., AND ALVINO, C. The piecewise smooth mumfordshah function on an arbitrary graph. IEEE Transactions on Image Processing 18, 11, 2547-2561; [10] GRADY, L., AND SCHWARTZ, E. L. 2006. Isoperimetric graph partitioning for image segmentation. IEEE Transactions on Pattern Analysis and Machine Intelligence 28, 3 (March), 469-475; [11] GRADY, L., SINGH, V., KOHLBERGER, T., ALVINO, C., AND BAHLMANN, C. 2012. Automatic segmentation of unknown objects, with application to baggage security. In European Conference on Computer Vision (ECCV); [12] GRIMM, S., BRUCKNER, S., KANITSAR, A., AND GRÖLLER, M. E., 2004. Flexible direct multi-volume rendering in interactive scenes, October; [13] HADWIGER, M., BERGER, C., AND HAUSER, H. 2003. High quality two-level volume rendering of segmented data sets on consumer graphics hardware. Visualization, 301-308; [14] KAINZ, B., GRABNER, M., BORNIK, A., HAUSWIESNER, S., MUEHL, J., AND SCHMALSTIEG, D. 2009. Ray casting of multiple volumetric datasets with polyhedral boundaries on manycore gpus. In ACM SIGGRAPH Asia, 152:1-152:9; [15] LI, W., AGRAWALA, M., CURLESS, B., AND SALESIN, D. 2008. Automated generation of interactive 3d exploded view diagrams. In ACM SIGGRAPH, 101:1-101:7; [16] LI, W. 2010. Multi-layer volume ray casting on gpu. In Volume Graphics, 5-12. [17] NAGY, Z., AND KLEIN, R. 2003. Depth-peeling for texture-based volume rendering. In Pacific Graphics, 429; and [18] ZHOU, J., AND TAKATSUKA, M. 2009. Automatic transfer function generation using contour tree controlled residue flow model and color harmonics. IEEE Transactions on Visualization and Computer Graphics 15, 6 (November), 1481-1488.

While there have been shown, described and pointed out fundamental novel features of the invention as applied to preferred embodiments thereof, it will be understood that various omissions and substitutions and changes in the form and details of the methods and systems illustrated and in its operation may be made by those skilled in the art without departing from the spirit of the invention. It is the intention, therefore, to be limited only as indicated by the claims.

The invention claimed is:

1. A method to virtually unpack a piece of luggage, comprising:
    scanning the piece of luggage to obtain three-dimensional (3D) volumetric data of a plurality of objects in a packed state inside the piece of luggage;
    processing the 3D volumetric data to segment the plurality of objects in the packed state into a plurality of 3D volume objects corresponding to the plurality of packed objects;
    rendering each of the plurality of 3D volume objects in an unpacked state to be simultaneously displayed on the display by:
    determining a state of occlusion of each of the plurality of 3D volume objects when in the packed state relative to a viewing direction, wherein the state of occlusion includes an occlusion value for each object that is indicative of the extent to which each object is blocked from unpacking by other objects;
    determining an unpacking order to move the plurality of 3D volume objects based on the determined state of occlusion of the plurality of 3D volume objects; and
    outputting an animation on the display in which each of the plurality of 3D volume objects in the determined unpacking order moves spatially out of the packed state into the unpacked state.

2. The method of claim 1, further comprising storing in a memory a rendered image of each of the plurality of unpacked 3D volume objects as an individually retrievable sprite.

3. The method of claim 1, further comprising: segmenting the plurality of packed objects from the 3D volumetric data to create a plurality of binary label volumes corresponding to the packed objects; and
    combining the binary volumes to form a label volume with a voxel storing an identification (ID) value of a corresponding binary label volume.

4. The method of claim 1, further comprising:
    generating an assignment of colors to each segmented object by computing an interference map from object identification (ID) images.

5. The method of claim 4, wherein the interference map is calculated by the processor through a 2D filtering by evaluating an expression:

$$\min_{layer(pA) \le LT \wedge layer(pB) \le LT} (DIST(Pa, Pb)) \le DT,$$

with
    pA and pB representing pixels in an image projected from front faces of objects A and B respectively,
    dist(pA, pB) represents a distance between the two pixels in image space,
    DT is a predetermined distance threshold,
    layer(p) represents a layer index of pixel p, and
    LT restricts computation to LT layers, and
    utilizing a graph coloring algorithm to assign a different hue to each interfering objects in the interference map.

6. The method of claim 4, further comprising:
    applying the object ID images of a plurality of segmented objects to determine the unpacking order based on an occlusion ratio of each object from the determined viewing direction.

7. The method of claim 1, wherein an unpacking scene is rendered by accessing at least three rendering layers, wherein
    a first layer containing a rendered image of all objects that are in a packed state;
    a second layer containing a rendered image of an object being unpacked; and
    a third layer containing rendered images of sprites of unpacked objects.

8. A system to display virtually unpacking of luggage containing a plurality of objects in a packed state, comprising:
    a luggage scanner configured to obtain three-dimensional (3D) volumetric data of the plurality of objects in the packed state inside the luggage;
    a memory enabled to store data and instructions;
    a display; and
    a processor enabled to access the memory to obtain data and instructions, the processor enabled to execute instructions to
    access the 3D volumetric data generated by the luggage scanner,
    process the 3D volumetric data to segment the plurality of objects in the packed state into a plurality of 3D volume objects corresponding to the plurality of packed objects,
    and render each of the plurality of 3D volume objects in an unpacked state simultaneously displayed on the display by
    determining an unpacking order to move the plurality of 3D volume objects based on a determined state of occlusion of the plurality of 3D volume objects, wherein the state of occlusion includes an occlusion value for each object that is indicative of the extent to which each object is blocked from unpacking by other objects, and
    based on the determined unpacking order outputting an animation on the display in which each of the plurality of 3D volume objects in the determined unpacking order moves spatially out of the packed state into the unpacked state.

9. The system of claim 8,
    wherein the processor is operable to segment the plurality of objects in the packed state from the 3D volumetric data to create a plurality of binary label volumes corresponding to the plurality of objects in the packed state,
    and to combine the binary volumes to form a label volume with a voxel storing an identification (ID) value of a corresponding binary label volume.

10. The system of claim 8,
    wherein the processor is operable to generate an assignment of colors to each segmented object by computing an interference map from object identification (ID) images.

11. The system of claim 10,
wherein the processor is operable to generate an interference map from object ID images through a 2D filtering by evaluating an expression:

$$\min_{layer(pA) \leq LT \wedge layer(pB) \leq LT} (DIST(Pa, Pb)) \leq DT,$$

with
- pA and pB representing pixels in an image projected from front faces of objects A and B respectively,
- dist(pA, pB) represents a distance between the two pixels in image space,
- DT is a predetermined distance threshold,
- layer(p) represents a layer index of pixel p, and
- LT restricts computation to LT layers, and utilizing a graph coloring algorithm to assign a different hue to each interfering objects in the interference map.

12. The system of claim 10, wherein the processor is operable to apply the object ID images of the plurality of segmented objects to determine the unpacking order based on an occlusion ratio of each object relative to the viewing direction.

13. The system of claim 8, further comprising a display to render the unpacking as an animated series of images.

14. The system of claim 8, wherein the processor is operable to render an unpacking scene by accessing at least three rendering layers, wherein
- a first layer contains a rendered image of all objects that are in a packed state;
- a second layer contains a rendered image of an object being unpacked; and
- a third layer contains rendered images of sprites of unpacked objects.

15. The system of claim 8, wherein images of unpacked objects are animated in an order that displays a repacking of the objects in the unpacked state to the plurality of objects in the packed state.

16. A method for visually unpacking on a display three-dimensional (3D) volumetric data of a plurality of objects in a packed state into a plurality of unpacked objects, comprising:
- processing the 3D volumetric data to segment the plurality of objects in the packed state into a plurality of 3D volume objects corresponding to the plurality of packed objects;
- displaying the luggage including the 3D volume objects in the packed state on the display; and
- rendering each of the plurality of 3D volume objects in an unpacked state simultaneously displayed on the display by:
- determining a viewing direction corresponding to an orientation at which the plurality of objects is viewable on the display with the 3D volume objects in the packed state;
- determining a state of occlusion of the plurality of 3D volume objects when in the packed state relative to the determined viewing direction, wherein the state of occlusion includes an occlusion value for each object that is indicative of the extent to which each object is blocked from unpacking by other objects;
- determining an unpacking order to move the plurality of 3D volume objects based on the determined state of occlusion of the plurality of 3D volume objects; and
- outputting an animation on the display in which each of the plurality of 3D volume objects in the determined unpacking order moves spatially out of the packed state into the unpacked state.

17. The method of claim 16, wherein the plurality of 3D volume objects are unpacked in the unpacking direction corresponding to a direction opposite the determined viewing direction.

18. The method of claim 16, wherein the method is applied in a luggage inspection system.

* * * * *